United States Patent
Powell et al.

(10) Patent No.: US 9,242,912 B2
(45) Date of Patent: Jan. 26, 2016

(54) METHODS AND SYSTEMS EMPLOYING AN INCLINED DIGESTION UNIT FOR HYDROTHERMAL DIGESTION OF CELLULOSIC BIOMASS SOLIDS

(71) Applicant: SHELL OIL COMPANY, Houston, TX (US)

(72) Inventors: Joseph Broun Powell, Houston, TX (US); Alouisius Nicolaas Renee Bos, Amsterdam (NL); Peter Anton August Klusener, Amsterdam (NL); Ingmar Hubertus Josephina Ploemen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 14/264,647

(22) Filed: Apr. 29, 2014

(65) Prior Publication Data
US 2014/0330048 A1  Nov. 6, 2014

Related U.S. Application Data

(60) Provisional application No. 61/817,990, filed on May 1, 2013.

(51) Int. Cl.
| | |
|---|---|
| *C07C 29/09* | (2006.01) |
| *C08H 8/00* | (2010.01) |
| *C10G 1/06* | (2006.01) |
| *C10G 1/08* | (2006.01) |
| *C10G 1/00* | (2006.01) |
| *C10G 3/00* | (2006.01) |
| *C07B 41/00* | (2006.01) |

(52) U.S. Cl.
CPC ............... *C07C 29/09* (2013.01); *C07B 41/00* (2013.01); *C08H 8/00* (2013.01); *C10G 1/002* (2013.01); *C10G 1/006* (2013.01); *C10G 1/065* (2013.01); *C10G 1/08* (2013.01); *C10G 1/083* (2013.01); *C10G 3/42* (2013.01); *C10G 3/46* (2013.01); *C10G 3/48* (2013.01); *C10G 3/50* (2013.01); *C10G 3/55* (2013.01); *C10G 2300/1014* (2013.01)

(58) Field of Classification Search
None
See application file for complete search history.

(56) References Cited

U.S. PATENT DOCUMENTS

| | | |
|---|---|---|
| 2,966,215 A | 12/1960 | Durkee |
| 6,030,915 A | 2/2000 | De Boer |
| 6,127,299 A | 10/2000 | De Boer et al. |
| 2010/0236988 A1 | 9/2010 | Gabrielov et al. |
| 2011/0120663 A1 | 5/2011 | Engstrom et al. |
| 2012/0317872 A1 | 12/2012 | Powell et al. |
| 2013/0109896 A1 | 5/2013 | Powell et al. |
| 2014/0000153 A1 | 1/2014 | Powell |
| 2014/0005444 A1 | 1/2014 | Komplin et al. |
| 2014/0005445 A1 | 1/2014 | Komplin et al. |

FOREIGN PATENT DOCUMENTS

| | | |
|---|---|---|
| EP | 344462 | 12/1989 |
| WO | 9105907 | 5/1991 |

OTHER PUBLICATIONS

International Search Report dated Oct. 24, 2014 for PCT/US2014/035859 filed Apr. 29, 2014.

*Primary Examiner* — Brian J Davis

(57) ABSTRACT

Maintaining long residence times during hydrothermal digestion of cellulosic biomass solids may be complicated by a number of factors, including biomass compaction. Advantages in this regard may be realized by digesting cellulosic biomass solids in an inclined digestion unit. Such methods can comprise: introducing cellulosic biomass solids to a hydrothermal digestion unit comprising one or more inclined surfaces therein; introducing a fluid phase digestion medium containing a slurry catalyst to the hydrothermal digestion unit, the slurry catalyst being capable of activating molecular hydrogen; supplying an upwardly directed flow of molecular hydrogen from a source disposed along each inclined surface as the cellulosic biomass solids descend along each inclined surface; and heating the cellulosic biomass solids as they descend along each inclined surface in the presence of the slurry catalyst and the molecular hydrogen, thereby forming an alcoholic component derived from the cellulosic biomass solids.

32 Claims, 6 Drawing Sheets

METHODS AND SYSTEMS EMPLOYING AN INCLINED DIGESTION UNIT FOR HYDROTHERMAL DIGESTION OF CELLULOSIC BIOMASS SOLIDS

The present application claims the benefit of U.S. Patent Application No. 61/817,990 filed May 1, 2013, the entire disclosure of which is hereby incorporated by reference.

FIELD OF THE INVENTION

The present disclosure generally relates to digestion of cellulosic biomass solids, and, more specifically, to systems and methods in which cellulosic biomass solids may be processed in a hydrothermal digestion unit having one or more inclined surfaces present therein.

BACKGROUND OF THE INVENTION

A number of substances of commercial significance may be produced from natural sources, including biomass. Cellulosic biomass may be particularly advantageous in this regard due to the versatility of the abundant carbohydrates found therein in various forms. As used herein, the term "cellulosic biomass" refers to a living or recently living biological material that contains cellulose. The lignocellulosic material found in the cell walls of higher plants is the world's largest source of carbohydrates. Materials commonly produced from cellulosic biomass may include, for example, paper and pulpwood via partial digestion, and bioethanol by fermentation.

Plant cell walls are divided into two sections: primary cell walls and secondary cell walls. The primary cell wall provides structural support for expanding cells and contains three major polysaccharides (cellulose, pectin, and hemicellulose) and one group of glycoproteins. The secondary cell wall, which is produced after the cell has finished growing, also contains polysaccharides and is strengthened through polymeric lignin that is covalently crosslinked to hemicellulose. Hemicellulose and pectin are typically found in abundance, but cellulose is the predominant polysaccharide and the most abundant source of carbohydrates. The complex mixture of constituents that is co-present with the cellulose can make its processing difficult, as discussed hereinafter.

Significant attention has been placed on developing fossil fuel alternatives derived from renewable resources. Cellulosic biomass has garnered particular attention in this regard due to its abundance and the versatility of the various constituents found therein, particularly cellulose and other carbohydrates. Despite promise and intense interest, the development and implementation of bio-based fuel technology has been slow. Existing technologies have heretofore produced fuels having a low energy density (e.g., bioethanol) and/or that are not fully compatible with existing engine designs and transportation infrastructure (e.g., methanol, biodiesel, Fischer-Tropsch diesel, hydrogen, and methane). Moreover, conventional bio-based processes have typically produced intermediates in dilute aqueous solutions (>50% water by weight) that are difficult to further process. Energy- and cost-efficient processes for processing cellulosic biomass into fuel blends having similar compositions to fossil fuels would be highly desirable to address the foregoing issues and others.

When converting cellulosic biomass into fuel blends and other materials, cellulose and other complex carbohydrates therein can be extracted and transformed into simpler organic molecules, which can be further reformed thereafter. Fermentation is one process whereby complex carbohydrates from cellulosic biomass may be converted into a more usable form. However, fermentation processes are typically slow, require large volume reactors and high dilution conditions, and produce an initial reaction product having a low energy density (ethanol). Digestion is another way in which cellulose and other complex carbohydrates may be converted into a more usable form. Digestion processes can break down cellulose and other complex carbohydrates within cellulosic biomass into simpler, soluble carbohydrates that are suitable for further transformation through downstream reforming reactions. As used herein, the term "soluble carbohydrates" refers to monosaccharides or polysaccharides that become solubilized in a digestion process. Although the underlying chemistry is understood behind digesting cellulose and other complex carbohydrates and further transforming simple carbohydrates into organic compounds reminiscent of those present in fossil fuels, high-yield and energy-efficient digestion processes suitable for converting cellulosic biomass into fuel blends have yet to be developed. In this regard, the most basic requirement associated with converting cellulosic biomass into fuel blends using digestion and other processes is that the energy input needed to bring about the conversion should not be greater than the available energy output of the product fuel blends. This basic requirement leads to a number of secondary issues that collectively present an immense engineering challenge that has not been solved heretofore.

The issues associated with converting cellulosic biomass into fuel blends in an energy- and cost-efficient manner using digestion are not only complex, but they are entirely different than those that are encountered in the digestion processes commonly used in the paper and pulpwood industry. Since the intent of cellulosic biomass digestion in the paper and pulpwood industry is to retain a solid material (e.g., wood pulp), incomplete digestion is usually performed at low temperatures (e.g., less than about 100° C.) for a fairly short period of time. In contrast, digestion processes suitable for converting cellulosic biomass into fuel blends and other materials are ideally configured to maximize yields by solubilizing as much of the original cellulosic biomass charge as possible in a high-throughput manner. Paper and pulpwood digestion processes also typically remove lignin from the raw cellulosic biomass prior to pulp formation. Although digestion processes used in connection with forming fuel blends and other materials may likewise remove lignin prior to digestion, these extra process steps may impact the energy efficiency and cost of the biomass conversion process. The presence of lignin during high-conversion cellulosic biomass digestion may be particularly problematic in some instances.

Production of soluble carbohydrates for use in fuel blends and other materials via routine modification of paper and pulpwood digestion processes is not believed to be economically feasible for a number of reasons. Simply running the digestion processes of the paper and pulpwood industry for a longer period of time to produce more soluble carbohydrates is undesirable from a throughput standpoint. Use of digestion promoters such as strong alkalis, strong acids, or sulfites to accelerate the digestion rate can increase process costs and complexity due to post-processing separation steps and the possible need to protect downstream components from these agents. Accelerating the digestion rate by increasing the digestion temperature can actually reduce yields due to thermal degradation of soluble carbohydrates that can occur at elevated digestion temperatures, particularly over extended periods of time. Once produced by digestion, soluble carbohydrates are very reactive and can rapidly degrade to produce caramelans and other heavy ends degradation products, especially under higher temperature conditions, such as above about 150° C. Use of higher digestion temperatures can also be undesirable from an energy efficiency standpoint. Any of these difficulties can defeat the economic viability of fuel blends derived from cellulosic biomass.

One way in which soluble carbohydrates can be protected from thermal degradation is through subjecting them to one or more catalytic reduction reactions, which may include hydrogenation and/or hydrogenolysis reactions. Stabilizing soluble carbohydrates through conducting one or more catalytic reduction reactions may allow digestion of cellulosic biomass to take place at higher temperatures than would otherwise be possible without unduly sacrificing yields. Depending on the reaction conditions and catalyst used, reaction products formed as a result of conducting one or more catalytic reduction reactions on soluble carbohydrates may comprise one or more alcohol functional groups, particularly including triols, diols, monohydric alcohols, and any combination thereof, some of which may also include a residual carbonyl functionality (e.g., an aldehyde or a ketone). Such reaction products are more thermally stable than soluble carbohydrates and may be readily transformable into fuel blends and other materials through conducting one or more downstream reforming reactions. In addition, the foregoing types of reaction products are good solvents in which a hydrothermal digestion may be performed, thereby promoting solubilization of soluble carbohydrates as their reaction products during hydrothermal digestion.

A particularly effective manner in which soluble carbohydrates may be formed and converted into more stable compounds is through conducting the hydrothermal digestion of cellulosic biomass in the presence of molecular hydrogen and a slurry catalyst capable of activating the molecular hydrogen (also referred to herein as a "hydrogen-activating catalyst"). That is, in such approaches (termed "in situ catalytic reduction reaction processes" herein), the hydrothermal digestion of cellulosic biomass and the catalytic reduction of soluble carbohydrates produced therefrom may take place in the same vessel. As used herein, the term "slurry catalyst" will refer to a catalyst comprising fluidly mobile catalyst particles that can be at least partially suspended in a fluid phase via gas flow, liquid flow, mechanical agitation, or any combination thereof. If the slurry catalyst is sufficiently well distributed in the cellulosic biomass, soluble carbohydrates formed during hydrothermal digestion may be intercepted and converted into more stable compounds before they have had an opportunity to significantly degrade, even under thermal conditions that otherwise promote their degradation. Without adequate catalyst distribution being realized, soluble carbohydrates produced by in situ catalytic reduction reaction processes may still degrade before they have had an opportunity to encounter a catalytic site and undergo a stabilizing reaction. In situ catalytic reduction reaction processes may also be particularly advantageous from an energy efficiency standpoint, since hydrothermal digestion of cellulosic biomass is an endothermic process, whereas catalytic reduction reactions are exothermic. Thus, the excess heat generated by the in situ catalytic reduction reaction(s) may be utilized to drive the hydrothermal digestion with little opportunity for heat transfer loss to occur, thereby lowering the amount of additional heat energy input needed to conduct the digestion.

Another issue associated with the processing of cellulosic biomass into fuel blends and other materials is created by the need for high conversion percentages of a cellulosic biomass charge into soluble carbohydrates. Specifically, as cellulosic biomass solids are digested, their size gradually decreases to the point that they can become fluidly mobile. As used herein, cellulosic biomass solids that are fluidly mobile, particularly cellulosic biomass solids that are about 3 mm in size or less, will be referred to as "cellulosic biomass fines." Cellulosic biomass fines can be transported out of a digestion zone of a system for converting cellulosic biomass and into one or more zones where solids are unwanted and can be detrimental. For example, cellulosic biomass fines have the potential to plug catalyst beds, transfer lines, valving, and the like. Furthermore, although small in size, cellulosic biomass fines may represent a non-trivial fraction of the cellulosic biomass charge, and if they are not further converted into soluble carbohydrates, the ability to attain a satisfactory conversion percentage may be impacted. Since the digestion processes of the paper and pulpwood industry are run at relatively low cellulosic biomass conversion percentages, smaller amounts of cellulosic biomass fines are believed to be generated and have a lesser impact on those digestion processes.

In addition to the desired carbohydrates, other substances may be present within cellulosic biomass that can be especially problematic to deal with in an energy- and cost-efficient manner. Sulfur- and/or nitrogen-containing amino acids or other catalyst poisons may be present in cellulosic biomass. If not removed, these catalyst poisons can impact the catalytic reduction reaction(s) used to stabilize soluble carbohydrates, thereby resulting in process downtime for catalyst regeneration and/or replacement and reducing the overall energy efficiency when restarting the process. This issue is particularly significant for in situ catalytic reduction reaction processes, where there is minimal opportunity to address the presence of catalyst poisons, at least without significantly increasing process complexity and cost. As mentioned above, lignin can also be particularly problematic to deal with if it is not removed prior to beginning digestion. During cellulosic biomass processing, the significant quantities of lignin present in cellulosic biomass may lead to fouling of processing equipment, potentially leading to costly system down time. The significant lignin quantities can also lead to realization of a relatively low conversion of the cellulosic biomass into useable substances per unit weight of feedstock.

As evidenced by the foregoing, the efficient conversion of cellulosic biomass into fuel blends and other materials is a complex problem that presents immense engineering challenges. The present disclosure addresses these challenges and provides related advantages as well.

SUMMARY OF THE INVENTION

The present disclosure generally relates to digestion of cellulosic biomass solids, and, more specifically, to systems and methods in which cellulosic biomass solids may be processed in a hydrothermal digestion unit having one or more inclined surfaces present therein.

In some embodiments, the present disclosure provides methods comprising: introducing cellulosic biomass solids to a hydrothermal digestion unit comprising one or more inclined surfaces therein; introducing a fluid phase digestion medium containing a slurry catalyst to the hydrothermal digestion unit, the slurry catalyst being capable of activating molecular hydrogen; wherein, once introduced to the hydrothermal digestion unit, the cellulosic biomass solids, the fluid phase digestion medium, and the slurry catalyst descend along the one or more inclined surfaces; supplying an upwardly directed flow of molecular hydrogen through the cellulosic biomass solids as they descend along the one or more inclined surfaces, the upwardly directed flow of molecular hydrogen being supplied from a source disposed along each inclined surface; and heating the cellulosic biomass solids as they descend along the one or more inclined surfaces in the presence of the slurry catalyst and the molecular hydrogen, thereby forming an alcoholic component derived from the cellulosic biomass solids.

In some embodiments, the present disclosure provides methods comprising: introducing cellulosic biomass solids to a hydrothermal digestion unit comprising a plurality of inclined tubular elements that are fluidly connected to one another in series and vertically spaced apart from one another; introducing a fluid phase digestion medium containing a slurry catalyst to the hydrothermal digestion unit, the slurry catalyst being capable of activating molecular hydrogen; wherein, once introduced to the hydrothermal digestion unit, the cellulosic biomass solids, the fluid phase digestion medium, and the slurry catalyst descend along the inclined tubular elements; supplying an upwardly directed flow of molecular hydrogen through the cellulosic biomass solids as they descend along the inclined tubular elements, the upwardly directed flow of molecular hydrogen being supplied from a source disposed longitudinally along each inclined tubular element; transferring molecular hydrogen from a lower inclined tubular element to an upper inclined tubular element; and heating the cellulosic biomass solids as they descend along the inclined tubular elements in the presence of the slurry catalyst and the molecular hydrogen, thereby forming an alcoholic component derived from the cellulosic biomass solids.

In some embodiments, the present disclosure provides biomass conversion systems comprising: a hydrothermal digestion unit comprising: a plurality of inclined tubular elements that are fluidly connected to one another in series and vertically spaced apart from one another; a vertical fluid connection adjoining an upper inclined tubular element to a lower inclined tubular element; and a gas distribution system longitudinally disposed within each inclined tubular element along its length; and a fluid conduit configured to establish fluid communication between a lowermost inclined tubular element and an uppermost inclined tubular element.

The features and advantages of the present disclosure will be readily apparent to one having ordinary skill in the art upon a reading of the description of the embodiments that follows.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to one having ordinary skill in the art and the benefit of this disclosure.

DETAILED DESCRIPTION

Figure 1:
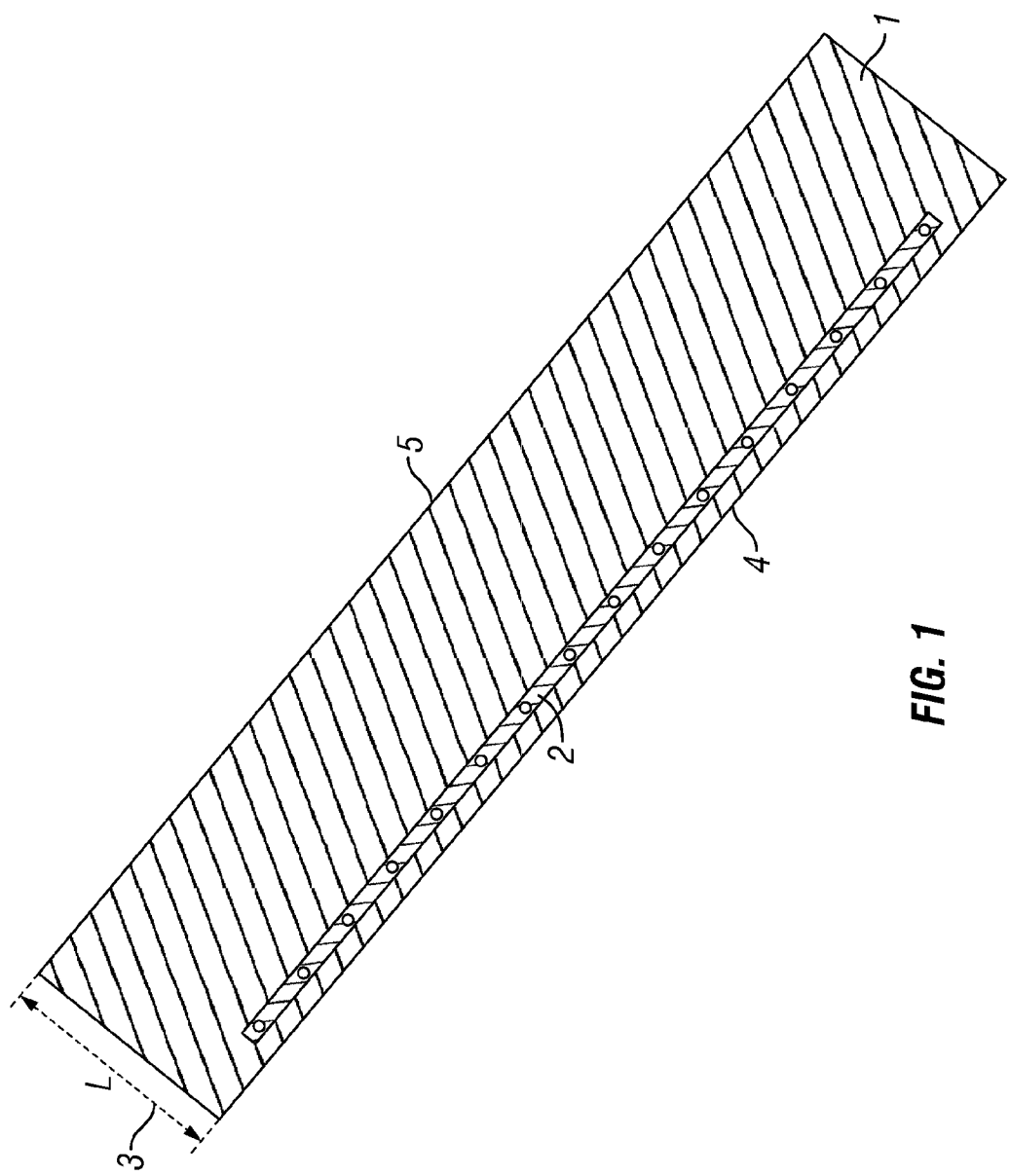
FIG. 1 shows an illustrative schematic of an inclined tubular element having a gas distribution system longitudinally disposed therein.

The present disclosure generally relates to digestion of cellulosic biomass solids, and, more specifically, to systems and methods in which cellulosic biomass solids may be processed in a hydrothermal digestion unit having one or more inclined surfaces present therein.

In the embodiments described herein, the digestion rate of cellulosic biomass solids may be accelerated in the presence of a fluid phase digestion medium comprising a digestion solvent. In some instances, the fluid phase digestion medium may be maintained at elevated pressures that keep the digestion solvent in a liquid state when raised above its normal boiling point. Although the more rapid digestion rate of cellulosic biomass solids under elevated temperature and pressure conditions may be desirable from a throughput standpoint, soluble carbohydrates may be susceptible to degradation at elevated temperatures, as discussed above. As further discussed above, one approach for addressing the degradation of soluble carbohydrates during hydrothermal digestion is to conduct an in situ catalytic reduction reaction process so as to convert the soluble carbohydrates into more stable compounds as soon as possible after their formation.

Although digesting cellulosic biomass solids by an in situ catalytic reduction reaction process may be particularly advantageous for at least the reasons noted above, successfully executing such a coupled approach may be problematic in other aspects. One significant issue that may be encountered is that of adequate catalyst distribution within the digesting cellulosic biomass solids, since insufficient catalyst distribution can result in poor stabilization of soluble carbohydrates. The present inventors discovered that, in certain instances, a slurry catalyst may be effectively distributed from the bottom of a charge of cellulosic biomass solids to the top using upwardly directed fluid flow to fluidize and upwardly convey slurry catalyst particulates into the interstitial spaces within the charge. Suitable techniques for using fluid flow to distribute a slurry catalyst within cellulosic biomass solids in such a manner are described in commonly owned US20140005445 and US20140005444 and incorporated herein by reference in its entirety. In addition to affecting distribution of the slurry catalyst, upwardly directed fluid flow may promote expansion of the cellulosic biomass solids and disfavor gravity-induced compaction that occurs during their addition and digestion, particularly as the digestion process proceeds and their structural integrity decreases. Such approaches may also address the problem of cellulosic biomass fines, since they may be co-flowed with the motive fluid.

Effective distribution of molecular hydrogen within cellulosic biomass solids during hydrothermal digestion can also be problematic, as described in commonly owned U.S. Patent Applications 61/740006 and 61/740039, each filed on filed on Dec. 20, 2012 and incorporated herein by reference in its entirety. As with a poorly distributed slurry catalyst, inadequate distribution of molecular hydrogen in cellulosic biomass solids can likewise result in poor stabilization of soluble carbohydrates during in situ catalytic reduction reaction processes. Without being bound by any theory or mechanism, it is believed that a poor distribution of molecular hydrogen within cellulosic biomass solids may be realized due to a coalescence of introduced molecular hydrogen into large bubbles that are unable to penetrate into the interstitial spaces within a charge of digesting cellulosic biomass solids. As the vertical height of a charge of cellulosic biomass solids in contact with a continuous liquid phase increases, the propensity toward hydrogen bubble coalescence may be increased.

The present inventors recognized that the problems of biomass compaction and molecular hydrogen distribution might be simultaneously addressed by altering the configuration of a hydrothermal digestion unit being used to digest cellulosic biomass solids from a substantially vertical configuration into a configuration having one or more inclined surfaces therein. In some instances, such configurations will be referred to herein as "inclined digestion units." By digesting a charge of cellulosic biomass solids on an inclined surface, the thickness of the charge may be more limited than in an equivalent vertical configuration, such that there is a reduced likelihood of hydrogen bubble coalescence taking place. More particularly, molecular hydrogen provided from a source disposed along each inclined surface may become distributed in the cellulosic biomass solids while they descend along the surface. Furthermore, when molecular hydrogen is introduced to the cellulosic biomass solids in the foregoing manner, the upflow of molecular hydrogen may be more likely to maintain an effective slurry catalyst distribution than would be possible when fluidizing the slurry catalyst through a thicker charge of cellulosic biomass solids, such as in a vertically configured hydrothermal digestion unit.

In addition to better promoting the distribution of a slurry catalyst and molecular hydrogen in cellulosic biomass solids during hydrothermal digestion, an inclined digestion unit may also better address the problem of biomass compaction. In a vertically configured hydrothermal digestion unit, as the vertical height of a charge of cellulosic biomass solids increases, the lower portions of the charge can become compacted by the weight of the upper portions of the charge. This problem can be particularly significant as the hydrothermal digestion process progresses and the structural integrity of the cellulosic biomass solids decreases, leading to formation of a mush-like state, in which it is difficult to distribute a slurry catalyst and molecular hydrogen due to a reduced access to interstitial spaces therein. In contrast, by conducting the hydrothermal digestion of cellulosic biomass solids in a non-vertical configuration, compaction forces on the lower portions of the cellulosic biomass solids may be conferred to the inclined surface of the hydrothermal digestion unit, thereby lowering the likelihood of excessive compaction.

Further advantages may be realized by utilizing an inclined digestion unit as well. For a fixed vertical height, an inclined digestion unit may provide a longer digestion medium contact time than does a vertically configured digestion unit. In addition, aviation safety restrictions may place vertical height limitations on refinery components that can limit their throughput in commercial operations. An inclined digestion unit may meet aviation restrictions without sacrificing throughput capabilities. Finally, movement of cellulosic biomass solids and the digestion medium through the hydrothermal digestion unit may be aided by gravity, as they progress down the inclined surface therein.

In addition to the foregoing advantages, an inclined digestion unit may remain compatible with techniques used for addressing the formation of heterogeneous liquid phases during hydrothermal digestion of cellulosic biomass solids. While digesting cellulosic biomass solids by an in situ catalytic reduction reaction process in the presence of a slurry catalyst and an aqueous phase digestion solvent, where the cellulosic biomass solids were supplied on an ongoing basis, the present inventors discovered that lignin from the cellulosic biomass solids eventually separated as a phenolics liquid phase that was neither fully dissolved nor fully precipitated, but instead formed as a discrete liquid phase that was highly viscous and hydrophobic. The slurry catalyst was well wetted by the phenolics liquid phase and accumulated therein over time, thereby making the slurry catalyst less readily distributable in the cellulosic biomass solids (e.g., by using upwardly directed fluid flow). In many instances, the phenolics liquid phase was located below the aqueous phase, which also contained an alcoholic component derived from the cellulosic biomass solids via a catalytic reduction reaction of soluble carbohydrates. Depending on the ratio of water and organic solvent in the digestion solvent, rates of fluid flow, catalyst identity, reaction times and temperatures, and the like, a light organics phase was also sometimes observed, typically located above the aqueous phase, where the components of the light organics phase were also derived, at least in part, from the cellulosic materials in the biomass. Components present in the light organics phase included, for example, the alcoholic component derived from the cellulosic biomass solids, including $C_4$ or greater alcohols, and self-condensation products, such as those obtained by the acid-catalyzed Aldol reaction. The alcoholic component in the resulting two- or three-phase liquid mixture may be processed as described in more detail in commonly owned U.S. Patent Applications 61/720689 and 61/720747, each filed on Oct. 31, 2012 and incorporated herein by reference in its entirety.

Techniques for mitigating the accumulation of a slurry catalyst in a phenolics liquid phase are described in more detail in commonly owned U.S. Patent Application 61/720757, filed on Oct. 31, 2012 and incorporated herein by reference in its entirety. As described therein, the accumulated slurry catalyst within the phenolics liquid phase may be conveyed from a lower portion of the hydrothermal digestion unit to a location above the cellulosic biomass solids and released, such that the slurry catalyst then contacts the cellulosic biomass solids. By conveying the accumulated slurry catalyst in such a manner, the slurry catalyst may become redistributed in the cellulosic biomass solids as the phenolics liquid phase percolates downward through the cellulosic biomass solids, rather than from becoming distributed via upwardly directed fluid flow. As described herein, such techniques may be practiced in a similar manner when hydrothermal digestion is performed using an inclined digestion unit.

Unless otherwise specified, it is to be understood that use of the terms "biomass" or "cellulosic biomass" in the description herein refers to "cellulosic biomass solids." Solids may be in any size, shape, or form. The cellulosic biomass solids may be natively present in any of these solid sizes, shapes, or forms, or they may be further processed prior to hydrothermal digestion. In some embodiments, the cellulosic biomass solids may be chopped, ground, shredded, pulverized, and the like to produce a desired size prior to hydrothermal digestion. In some or other embodiments, the cellulosic biomass solids may be washed (e.g., with water, an acid, a base, combinations thereof, and the like) prior to hydrothermal digestion taking place.

In practicing the present embodiments, any type of suitable cellulosic biomass source may be used. Suitable cellulosic biomass sources may include, for example, forestry residues, agricultural residues, herbaceous material, municipal solid wastes, waste and recycled paper, pulp and paper mill residues, and any combination thereof. Thus, in some embodiments, a suitable cellulosic biomass may include, for example, corn stover, straw, bagasse, miscanthus, sorghum residue, switch grass, bamboo, water hyacinth, hardwood, hardwood chips, hardwood pulp, softwood, softwood chips, softwood pulp, and any combination thereof. Leaves, roots, seeds, stalks, husks, and the like may be used as a source of the cellulosic biomass. Common sources of cellulosic biomass may include, for example, agricultural wastes (e.g., corn stalks, straw, seed hulls, sugarcane leavings, nut shells, and the like), wood materials (e.g., wood or bark, sawdust, timber slash, mill scrap, and the like), municipal waste (e.g., waste paper, yard clippings or debris, and the like), and energy crops (e.g., poplars, willows, switch grass, alfalfa, prairie bluestream, corn, soybeans, and the like). The cellulosic biomass may be chosen based upon considerations such as, for example, cellulose and/or hemicellulose content, lignin content, growing time/season, growing location/transportation cost, growing costs, harvesting costs, and the like.

Illustrative carbohydrates that may be present in cellulosic biomass solids include, for example, sugars, sugar alcohols, celluloses, lignocelluloses, hemicelluloses, and any combination thereof. Once soluble carbohydrates have been produced through hydrothermal digestion according to the embodiments described herein, the soluble carbohydrates may be transformed into a more stable reaction product comprising a monohydric alcohol, a glycol, a triol, or any combination thereof, at least some of which may also contain a carbonyl functionality. As used herein, the term "glycol" will refer to compounds containing two alcohol functional groups, two alcohol functional groups and a carbonyl functionality, or any combination thereof. As used herein, the term "carbonyl functionality" will refer to an aldehyde functionality or a ketone functionality. As used herein, the term "triol" will refer to compounds containing three alcohol functional groups, three alcohol functional groups and a carbonyl functionality, and any combination thereof. As used herein, the term "monohydric alcohol" will refer to compounds containing one alcohol functional group, one alcohol functional group and a carbonyl functionality, and any combination thereof.

As used herein, the term "phenolics liquid phase" will refer to a fluid phase comprising liquefied lignin. In some embodiments, the phenolics liquid phase may be more dense than water, but it may also be less dense than water depending on lignin concentrations and the presence of other components, for example.

As used herein, the term "alcoholic component" will refer to a monohydric alcohol, glycol, triol, or any combination thereof that is formed from a catalytic reduction reaction of soluble carbohydrates derived from cellulosic biomass solids.

As used herein, the term "light organics phase" will refer to a fluid phase that is typically less dense than water and comprises an organic compound. The organic compound may include at least a portion of the alcoholic component formed via catalytic reduction of soluble carbohydrates, which may include $C_4$ or greater alcohols and self-condensation products thereof.

As used herein, the terms "inclined," "incline," "inclination" and other grammatical forms thereof will refer to a surface oriented at an angle of between about 5 degrees and about 85 degrees relative to horizontal.

As used herein, the term "vertical" will refer to a surface or structure oriented at an angle of between about 85 degrees and about 90 degrees relative to horizontal.

As used herein, the term "longitudinally" will refer to a lengthwise disposition along an elongated surface.

As used herein, the term "tubular" will refer to an elongated three-dimensional structure having an open space therein. Any number of surfaces may be present within the open space within the interior of the tubular structure. That is, the term "tubular" may be used to refer to both cylindrical and prismatic elongated three-dimensional structures. In embodiments where a tubular structure is cylindrical, it may have a length that is greater than its diameter.

As used herein, the term "upwardly directed" will refer to a direction of fluid flow from an inclined surface that is non-parallel to the surface.

In some embodiments, methods described herein can comprise: introducing cellulosic biomass solids to a hydrothermal digestion unit comprising one or more inclined surfaces therein; introducing a fluid phase digestion medium containing a slurry catalyst to the hydrothermal digestion unit, the slurry catalyst being capable of activating molecular hydrogen; wherein, once introduced to the hydrothermal digestion unit, the cellulosic biomass solids, the fluid phase digestion medium, and the slurry catalyst descend along the one or more inclined surfaces; supplying an upwardly directed flow of molecular hydrogen through the cellulosic biomass solids as they descend along the one or more inclined surfaces, the upwardly directed flow of molecular hydrogen being supplied from a source disposed along each inclined surface; and heating the cellulosic biomass solids as they descend along the one or more inclined surfaces in the presence of the slurry catalyst and the molecular hydrogen, thereby forming an alcoholic component derived from the cellulosic biomass solids.

The number of inclined surfaces that may be present in the hydrothermal digestion unit is not believed to be particularly limited. In some embodiments, there may be one inclined surface present in the hydrothermal digestion unit. In other embodiments, there may be two inclined surfaces, or three inclined surfaces, or four inclined surfaces, or five inclined surfaces, or six inclined surfaces, or seven inclined surfaces, or eight inclined surfaces, or nine inclined surfaces, or ten inclined surfaces. In some embodiments, the inclined surfaces may be present in an inclined tubular element, where the inclined tubular element is not believed to be particularly limited in geometric shape. When more than one inclined tubular element is present, the inclined tubular elements may be fluidly connected to one another in series. That is, in such embodiments, the inclined tubular elements may be connected head-to-tail, such that a lower portion of an upper inclined tubular element is fluidly connected to an upper portion of a lower inclined tubular element. In some or other embodiments, two or more inclined tubular elements may be oriented in parallel within the hydrothermal digestion unit.

In various embodiments, the one or more inclined surfaces or inclined tubular elements may be inclined at an angle ranging between about 5 degrees and about 85 degrees relative to horizontal. When multiple inclined surfaces or inclined tubular elements are present, they may be inclined at substantially the same angle, or some may be inclined at different angles. In some embodiments, the inclined surfaces or inclined tubular elements may be inclined at an angle ranging between about 5 degrees and about 10 degrees relative to horizontal, or at an angle ranging between about 10 degrees and about 15 degrees relative to horizontal, or at an angle ranging between about 15 degrees and about 20 degrees relative to horizontal, or at an angle ranging between about 20 degrees and about 25 degrees relative to horizontal, or at an angle ranging between about 25 degrees and about 30 degrees relative to horizontal, or at an angle ranging between about 30 degrees and about 35 degrees relative to horizontal, or at an angle ranging between about 35 degrees and about 40 degrees relative to horizontal, or at an angle ranging between about 40 degrees and about 45 degrees relative to horizontal, or at an angle ranging between about 45 degrees and about 50 degrees relative to horizontal, or at an angle ranging between about 50 degrees and about 55 degrees relative to horizontal, or at an angle ranging between about 55 degrees and about 60 degrees relative to horizontal, or at an angle ranging between about 60 degrees and about 65 degrees relative to horizontal, or at an angle ranging between about 65 degrees and about 70 degrees relative to horizontal, or at an angle ranging between about 70 degrees and about 75 degrees relative to horizontal, or at an angle ranging between about 75 degrees and about 80 degrees relative to horizontal, or at an angle ranging between about 80 degrees and about 85 degrees relative to horizontal. Choice of an appropriate angle of inclination for a given application may be determined by one having ordinary skill in the art given the benefit of the present disclosure. Factors that may be considered when choosing an angle of inclination for the inclined surface may include, for example, the coefficient of static fraction of cellulosic biomass solids on the inclined surface and the desired migration rate thereof within the hydrothermal digestion unit.

In some embodiments, a plurality of inclined tubular elements may be present in the hydrothermal digestion unit, where the inclined tubular elements may be fluidly connected to one another in series and vertically spaced apart from one another. By vertically spacing the inclined tubular elements apart from one another, there can be a transition zone located between each inclined tubular element. More specifically, in such embodiments, the hydrothermal digestion unit may further comprise a vertical fluid connection adjoining an upper inclined tubular element to a lower inclined tubular element. For example, a vertical fluid connection may establish fluid communication between a lowermost location of an upper inclined tubular element to an uppermost location of a lower inclined tubular element. As discussed hereinafter, vertical fluid connections may not only be used to establish fluid communication between two inclined tubular elements, but they may also provide a convenient location for withdrawing molecular hydrogen from the hydrothermal digestion unit for recirculation therein.

In some embodiments, the upwardly directed flow of molecular hydrogen through the cellulosic biomass solids may be supplied from a gas distribution system that is disposed along a length of the inclined surface, upon which the cellulosic biomass solids descend. For example, in some embodiments, the upwardly directed flow of molecular hydrogen through the cellulosic biomass solids in each inclined tubular element may be supplied from a gas distribution system that is longitudinally disposed within each inclined tubular element along its length. More specifically, the gas distribution system may be longitudinally disposed on a surface of the inclined tubular element upon which the cellulosic biomass solids descend (i.e., the bottom surface of the inclined tubular element), thereby allowing molecular hydrogen introduced therefrom to percolate upward through the cellulosic biomass solids during their descent. In some embodiments, the gas distribution system may be offset from the surface at a distance of less than about half of the effective vessel diameter or width. As described above, molecular hydrogen so introduced may mediate stabilization of soluble carbohydrates both by serving as a reactant for a catalytic reduction reaction and promoting distribution of a slurry catalyst in the cellulosic biomass solids. Suitable gas distribution systems may include slotted distributors, manifolds, empty piping with an array of holes disposed thereon, sintered metal elements, collections of nozzles at a spacing effective to disperse a gas phase, other gas distribution manifolds, combinations thereof, and the like.

In some embodiments, more than one gas distribution system may be longitudinally disposed within each inclined tubular element, where each gas distribution system is supplied individually with a gas feed. By supplying molecular hydrogen to multiple gas distribution systems, one may avoid pressure drops at locales removed from the point of gas introduction to the gas distribution system.

In some embodiments, the gas distribution system may be located substantially parallel to the incline of each inclined surface or each inclined tubular element. For example, within each inclined tubular element, the gas distribution system may be located within the same portion of the inclined tubular element as are the cellulosic biomass solids during their descent. FIG. 1 shows an illustrative schematic of an inclined tubular element 1 having gas distribution system 2 longitudinally disposed therein. Referring still to FIG. 1, line 3 having length L, drawn normal to lower surface 4 of inclined tubular element 1, may intersect opposing surface 5. In embodiments in which there is no defined lower surface 4, such as in a cylindrical inclined tubular element 1, length L refers to the diameter of the cylinder. The gas distribution system may be located within the lower 50% of this length, and cellulosic biomass solids may progress along lower surface 4 of inclined tubular element 1. More specifically, in some embodiments, the gas distribution system may be located within the lower 50% of each inclined tubular element, as measured along a line extending normal to the incline and intersecting an opposing surface thereto. In some embodiments, the gas distribution system may be located within the lower 40% of the inclined tubular element, or within the lower 30% of the inclined tubular element, or within the lower 20% of the inclined tubular element, or within the lower 10% of the inclined tubular element, as measured in a comparable manner.

In some embodiments, molecular hydrogen being supplied to the gas distribution system may be supplied from a molecular hydrogen source external to the hydrothermal digestion unit. In some or other embodiments, the molecular hydrogen being supplied to the gas distribution system may be recirculated or recycled from one section of the hydrothermal digestion unit to another. More specifically, in some embodiments, the methods described herein may further comprise transferring molecular hydrogen from a lower inclined tubular element to an upper inclined tubular element (e.g., to the gas distribution system contained therein). Transferring molecular hydrogen from a lower inclined tubular element to an upper inclined tubular element in this manner may allow the molecular hydrogen that has collected in the headspace of the lower inclined tubular element and is no longer distributed in the cellulosic biomass solids to be redistributed in other cellulosic biomass solids, where it may once again promote stabilization of soluble carbohydrates. Redistribution from a lower inclined tubular element to an upper inclined tubular element, or from a lower to upper gas distribution mechanism within an inclined tubular element, can be accomplished using the natural buoyancy of molecular hydrogen relative to liquid and solids phases and therefore does not necessitate intermediate compression of the molecular hydrogen. It is also to be recognized, however, that the molecular hydrogen may be recirculated to the same inclined tubular element or to a lower inclined tubular element by compressing the molecular hydrogen or by using a gas entraining pump. Moreover, in related embodiments, molecular hydrogen may be transferred from the headspace of an uppermost inclined tubular element to a lowermost inclined tubular element or other lower inclined tubular element in order to realize similar advantages.

In some embodiments, a feed for the gas distribution system may enter the inclined tubular element at a level above that of the fluid phase digestion medium contained therein. Advantages of the feed entering the inclined tubular element in such a manner may include limiting the possibility of plugging the feed with the fluid phase digestion medium and the cellulosic biomass solids. If a gas is being fed to an upper gas distribution mechanism, it is often desirable to maintain a gas velocity sufficient to prevent a fluid phase from entering the gas distribution mechanism via the action of gravity on the fluid phase. If the gas distribution system fills with a fluid phase or a mixed fluid phase and solid phase, it will no longer be possible to distribute a gas therethrough in the absence of gas phase recompression. However, if a feed line to the gas distribution mechanism rises to an elevation higher than the maximum liquid elevation within the inclined tubular element before descending into the gas distribution mechanism located therein, then it is not possible for a fluid phase to flow into the gas distribution system when gas flow is stopped, thereby reducing the likelihood of plugging and lowering the needed gas flow rates. For example, in some embodiments, a gas distribution feed line may enter each inclined tubular element within the upper 20% of the inclined tubular element, as measured along a line extending normal to the incline and intersecting an opposing surface thereto, as generally described in more detail above.

In some embodiments, methods described herein may comprise: introducing cellulosic biomass solids to a hydrothermal digestion unit comprising a plurality of inclined tubular elements that are fluidly connected to one another in series and vertically spaced apart from one another; introducing a fluid phase digestion medium containing a slurry catalyst to the hydrothermal digestion unit, the slurry catalyst being capable of activating molecular hydrogen; wherein, once introduced to the hydrothermal digestion unit, the cellulosic biomass solids, the fluid phase digestion medium, and the slurry catalyst descend along the inclined tubular elements; supplying an upwardly directed flow of molecular hydrogen through the cellulosic biomass solids as they descend along the inclined tubular elements, the upwardly directed flow of molecular hydrogen being supplied from a source disposed longitudinally along each inclined tubular element; transferring molecular hydrogen from a lower inclined tubular element to an upper inclined tubular element; and heating the cellulosic biomass solids as they descend along the inclined tubular elements in the presence of the slurry catalyst and the molecular hydrogen, thereby forming an alcoholic component derived from the cellulosic biomass solids.

Before discussing other various aspects of the above methods, illustrative biomass conversion systems suitable for practicing the methods set forth herein will now be described in greater detail. In some embodiments, biomass conversion systems described herein may comprise: a hydrothermal digestion unit comprising: a plurality of inclined tubular elements that are fluidly connected to one another in series and vertically spaced apart from one another, a vertical fluid connection adjoining an upper inclined tubular element to a lower inclined tubular element, and a gas distribution system longitudinally disposed within each inclined tubular element along its length; and a fluid conduit configured to establish fluid communication between a lowermost inclined tubular element and an uppermost inclined tubular element. Further description of the location of the gas distribution system within each inclined tubular element is set forth in more detail above.

In some embodiments, the biomass conversion systems may further comprise a gas distribution feed line that is fluidly connected to the gas distribution system in each inclined tubular element. Further description of the location of the gas distribution feed line within each inclined tubular element is set forth in more detail above.

Figure 2:
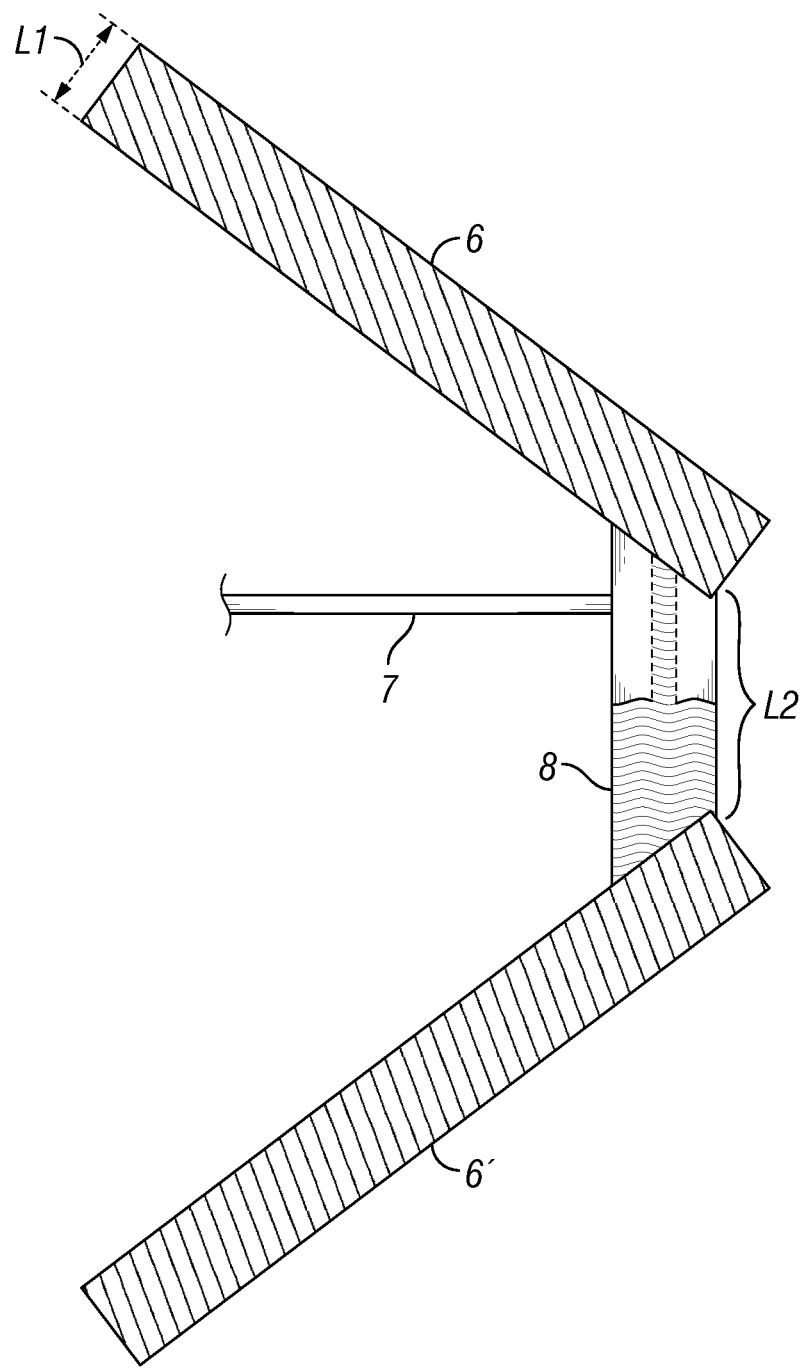
FIG. 2 shows an illustrative schematic of two inclined tubular elements fluidly connected in series by a vertical fluid connection.

In some embodiments, the biomass conversion systems may further comprise a gas recirculation line configured to establish fluid communication between a lower inclined tubular element and a gas distribution feed line in an upper inclined tubular element. In some embodiments, the gas recirculation line may be fluidly connected to the vertical fluid connection adjoining the upper inclined tubular element to the lower inclined tubular element. In some embodiments, the gas recirculation line may connect separate gas distribution mechanisms at different elevations within a single inclined tubular element, either from lower to upper elevations, or upper to lower elevations. Recirculating a gas from the vertical fluid connection may present particular advantages in certain embodiments. For example, if liquid levels are properly maintained in the hydrothermal digestion unit such that a liquid does not back up into the vertical fluid connection, the gas recirculation line may withdraw a gas (e.g., molecular hydrogen) from the vertical fluid connection without withdrawing a liquid therefrom. In some embodiments, a height of each vertical fluid connection may be greater than the cross-sectional width of an uppermost inclined tubular element to which it is adjoined. FIG. 2 shows an illustrative schematic of two inclined tubular elements 6 and 6' fluidly connected in series by vertical fluid connection 8. As depicted in FIG. 2, upper inclined tubular element 6 has a cross-sectional width $L_1$, and the height of vertical fluid connection 8 is $L_2$, where $L_2$ is greater than $L_1$. By having vertical fluid connection 8 sized in such a manner, gas recirculation line 7 may be fluidly connected thereto as depicted and allow a gas to be withdrawn therefrom without withdrawing a liquid from lower inclined tubular element 6'. This configuration limits the opportunity for backflow of liquids and/or solids to occur into the gas distribution system during upsets or stoppage of gas flow. A gas distribution system that is kept largely free of liquid and solids may effectively channel and redistribute the gas phase from bottom to top of the biomass conversion system using the natural buoyancy of the gas phase, without requiring mechanical energy input in the form of compression or other means.

In addition to the gas recirculation line configured to establish fluid communication between a lower inclined tubular element and a gas distribution feed line in an upper inclined tubular element, the biomass conversion systems may also further comprise a gas recycle line configured to establish fluid communication between the uppermost inclined tubular element and the lowermost inclined tubular element or any other lower inclined tubular element. This gas recycle line may be configured to convey a gas from the uppermost inclined tubular element to the lowermost inclined tubular element or any other lower inclined tubular element, thereby allowing a gas (e.g., molecular hydrogen) that has migrated to the top of the hydrothermal digestion unit to be returned to a lower location in the hydrothermal digestion unit, such as the lowermost inclined tubular element. Thus, this gas recycle line may establish a hydrogen circulation loop across the hydrothermal digestion unit. Although molecular hydrogen may be transferred between inclined tubular elements in the foregoing manner, it is to be recognized that in other embodiments, each inclined tubular element may be supplied with separate feeds of molecular hydrogen, if desired. In such embodiments, the excess molecular hydrogen exiting each inclined tubular element may be combined and then recirculated to one or more inclined tubular elements. Separate molecular hydrogen feeds may be desirable if hydrothermal digestion is conducted at different temperatures in each inclined tubular element, in which case, the rate of molecular hydrogen consumption may differ in each inclined tubular element.

In some embodiments, the biomass conversion systems may further comprise a biomass feed mechanism that is operatively coupled to an uppermost inclined tubular element, where the biomass feed mechanism is configured for addition of cellulosic biomass solids to the uppermost inclined tubular element while it is in a pressurized state (e.g., at least about 30 bar). Inclusion of the biomass feed mechanism may allow cellulosic biomass solids to be continuously or semi-continuously fed to the hydrothermal digestion unit, thereby allowing hydrothermal digestion to take place in a continual manner by replenishing cellulosic biomass solids that have been digested to form soluble carbohydrates. Suitable biomass feed mechanisms are described in greater detail hereinafter. Without the ability to introduce fresh cellulosic biomass solids to a pressurized hydrothermal digestion unit, depressurization and cooling of the hydrothermal digestion unit may take place during biomass addition, significantly reducing the energy- and cost-efficiency of the biomass conversion process. As used herein, the term "continuous addition" and grammatical equivalents thereof will refer to a process in which cellulosic biomass solids are added to a hydrothermal digestion unit in an uninterrupted manner without fully depressurizing the hydrothermal digestion unit. As used herein, the term "semi-continuous addition" and grammatical equivalents thereof will refer to a discontinuous, but as-needed, addition of cellulosic biomass solids to a hydrothermal digestion unit without fully depressurizing the hydrothermal digestion unit. Techniques through which cellulosic biomass solids may be added continuously or semi-continuously to a pressurized hydrothermal digestion unit are discussed in more detail hereinbelow.

In some embodiments, cellulosic biomass solids being continuously or semi-continuously added to the hydrothermal digestion unit may be pressurized before being added to the hydrothermal digestion unit, particularly when the hydrothermal digestion unit is in a pressurized state. Pressurization of the cellulosic biomass solids from atmospheric pressure to a pressurized state may take place in one or more pressurization zones before addition of the cellulosic biomass solids to the hydrothermal digestion unit. Suitable pressurization zones that may be used for pressurizing and introducing cellulosic biomass solids to a pressurized hydrothermal digestion unit are described in more detail in commonly owned US20130152457 and US20130152458 and incorporated herein by reference in its entirety. Suitable pressurization zones described therein may include, for example, pressure vessels, pressurized screw feeders, and the like. In some embodiments, multiple pressurization zones may be connected in series to increase the pressure of the cellulosic biomass solids in a stepwise manner. Pressurization may take place via addition of a gas or a liquid to the pressurization zone. In some embodiments, a liquid being used for pressurization may comprise a fluid phase that is transferred from the inclined tubular element. In other embodiments, instead of being recirculated to the inclined tubular element, a fluid phase may be diverted to the pressurization zone to affect its pressurization.

In some embodiments, the biomass conversion systems may further comprise a sump adjoined to the lowermost inclined tubular element at its lowermost point. The sump may collect a fluid phase that has completed its downward progression through the hydrothermal digestion unit or that has been formed in conjunction with the hydrothermal digestion process. In some embodiments, a fluid phase collected in the sump may be recirculated in the hydrothermal digestion unit. For example, in some embodiments, the fluid conduit described above may be fluidly connected to the sump. Any fluid phase in the sump may be recirculated therefrom. In some embodiments, an admixture of the fluid phase digestion medium and the slurry catalyst may be recirculated to an uppermost inclined tubular element via the fluid conduit. In some or other embodiments, a phenolics liquid phase and slurry catalyst accumulated therein may be recirculated to an uppermost inclined tubular element via the fluid conduit.

Various exemplary embodiments of the biomass conversion systems will now be further described with reference to the drawings. When like elements are used in one or more figures, identical reference characters will be used in each figure, and a detailed description of the element will be provided only at its first occurrence. Some features of the biomass conversion systems may be omitted in certain depicted configurations in the interest of clarity. Moreover, certain features such as, but not limited to pumps, valves, gas bleeds, gas inlets, fluid inlets, fluid outlets and the like have not necessarily been depicted in the figures, but their presence and function will be understood by one having ordinary skill in the art. In the figures, arrows have been drawn to depict the direction of liquid or gas flow. Moreover, gas transfer lines have been depicted in the figures as single lines, and liquid transfer lines have been depicted as conduits having two sides.

Figure 3:
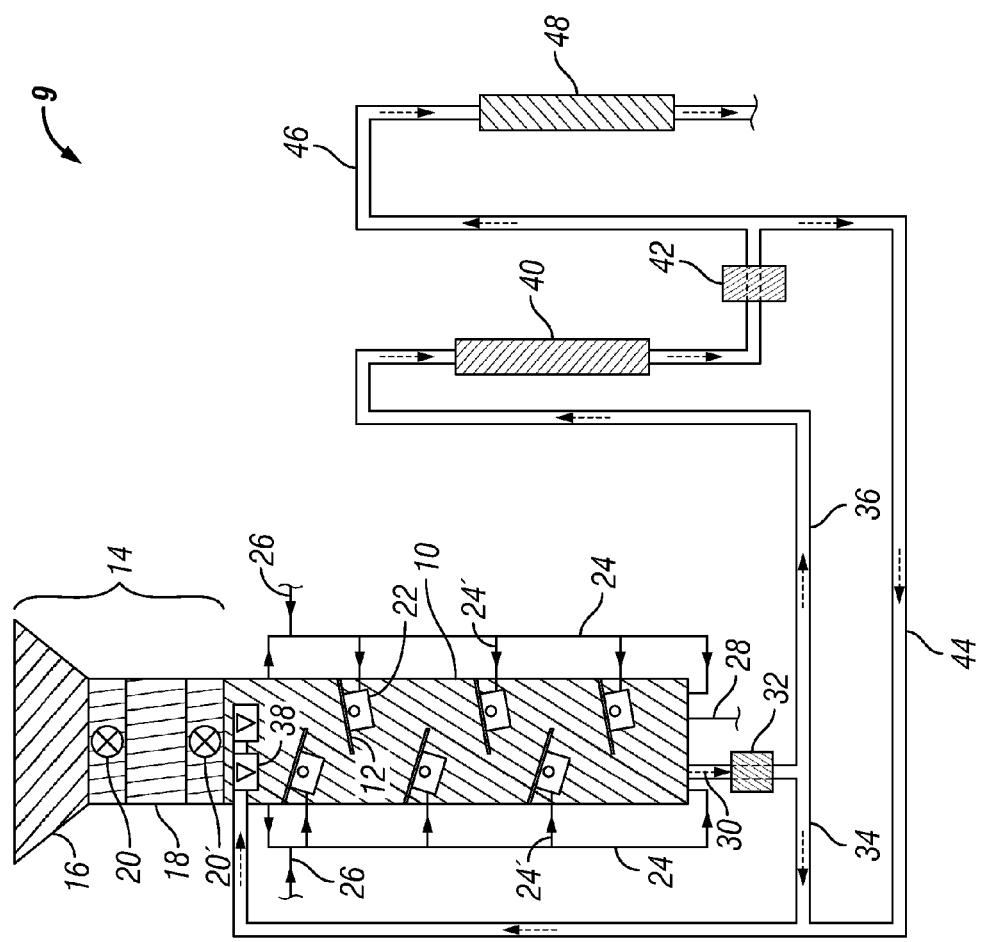
FIG. 3 shows an schematic of an illustrative biomass conversion system containing a vertically oriented hydrothermal digestion unit containing a plurality of inclined surfaces therein.

FIG. 3 shows an schematic of an illustrative biomass conversion system containing a vertically oriented hydrothermal digestion unit containing a plurality of inclined surfaces therein. As depicted in FIG. 3, biomass conversion system 9 contains hydrothermal digestion unit 10, which possesses inclined surfaces 12 therein. Although FIG. 3 has depicted inclined surfaces 12 as discrete entities configured in a "zigzag" pattern, it is to be recognized that inclined surfaces 12 may be present as a continuous inclined surface extending from near the top of hydrothermal digestion unit 10 to the bottom. For example, a continuous inclined surface may comprise a corkscrew or like spiral configuration disposed along the sidewalls of hydrothermal digestion unit 10.

Referring still to FIG. 3, solids introduction mechanism 14 may be operatively coupled to hydrothermal digestion unit 10. Solids introduction mechanism 14 may comprise loading mechanism 16 and pressure transition zone 18, which may elevate cellulosic biomass solids from atmospheric pressure to a pressure near that of the operating pressure of hydrothermal digestion unit 10, thereby allowing continuous or semi-continuous introduction of cellulosic biomass solids to take place without fully depressurizing hydrothermal digestion unit 10. Pressure isolation may be achieved with valves 20 and 20', which are operable for dispensation of cellulosic biomass solids therethrough. Suitable loading mechanisms and pressure transition zones have been described in more detail hereinabove.

Longitudinally disposed along the length of each inclined surface 12 is gas distribution mechanism 22, which may be configured to form gas bubbles in a fluid phase digestion medium contained within hydrothermal digestion unit 10. Each gas distribution mechanism 22 may be fluidly connected to gas distribution line 24 via gas distribution feed 24'. Although FIG. 3 has depicted two separate gas distribution lines 24 on opposing sides of hydrothermal digestion unit 10, it is to be recognized such depiction is for clarity purposes, and all gas distribution feeds 24' may emanate from a single gas distribution line 24, if desired. Gas distribution line 24 is configured to recycle a gas (e.g., molecular hydrogen) within hydrothermal digestion unit 10. Initial gas introduction or supplemental gas introduction may be made to gas distribution line 24 via line 26. Optionally or in addition to gas introduction via line 26, initial gas introduction or supplemental gas introduction may be made to hydrothermal digestion unit 10 via line 28, whereby upwardly directed gas flow may be established therein.

Also fluidly coupled to hydrothermal digestion unit 10 is fluid removal line 30, which may be fluidly coupled to separations unit 32. Fluid removal line 30 may be used to remove any fluid phase from hydrothermal digestion unit 10. Separations unit 32 may, for example, be used to separate a phenolics liquid phase from the fluid phase digestion medium, which contains an alcoholic component formed from cellulosic biomass solids. Separations unit 32 may employ any liquid-liquid or liquid-solid separation technique known to one having ordinary skill in the art. In the interest of simplicity, the FIGURES have depicted a single line exiting separations unit 32 and splitting into lines 34 and 36, but it is to be recognized that depending on the type of separation being performed and the eventual destination of the component being separated, multiple lines may emanate from separations unit 32. A fluid exiting separations unit 32 may be returned to hydrothermal digestion unit 10 via line 34 or removed therefrom via line 36 for further processing. Fluid being returned to hydrothermal digestion unit 10 via line 34 may include any fluid phase present or formed during the hydrothermal digestion of cellulosic biomass solids. In some embodiments, the fluid phase digestion medium and slurry catalyst may be conveyed in line 34. In some or other embodiments, a phenolics liquid phase and slurry catalyst accumulated therein may be conveyed in line 34. Although line 34 has been depicted as only a single fluid conduit, it is to be recognized that line 34 may comprise multiple lines if it is desired that a fluid phase digestion medium and a phenolics liquid phase be conveyed separately during their return to hydrothermal digestion unit 10. Once returned to hydrothermal digestion unit 10, a fluid in line 34 may pass through flow distribution mechanism 38. In various embodiments, flow distribution mechanism 38 may comprise sprayers, nozzles, slotted distributors, combinations thereof and the like in order to facilitate better contact of the fluid and/or slurry catalyst with cellulosic biomass solids being introduced to hydrothermal digestion unit 10.

The fluid exiting hydrothermal digestion unit 10 via line 30 may comprise a fluid phase digestion medium, which may contain an alcoholic component derived from cellulosic biomass solids. The alcoholic component may be further processed by the remaining components of biomass conversion system 9. Optionally, polishing reactor 40 may be fluidly coupled to hydrothermal digestion unit 10 via line 36. Polishing reactor 40 may contain a catalyst capable of activating molecular hydrogen, such that soluble carbohydrates being conveyed from hydrothermal digestion unit 10 may be further converted into an alcoholic component or the degree of oxygenation of the alcoholic component may be further decreased. Although not depicted in the FIGURES, an additional feed of molecular hydrogen may be supplied to polishing reactor 40. For example, in some embodiments, a glycol may be converted into a monohydric alcohol in polishing reactor 40. The catalyst present in polishing reactor 40 may be the same as or different than the slurry catalyst present in hydrothermal digestion unit 10. Thereafter, the alcoholic component may be conveyed to separations unit 42, where various operations may take place. Again, any suitable liquid-liquid separation technique known in the art may be employed in separations unit 42. In the interest of simplicity, the FIGURES have depicted a single line exiting separations unit 42 and splitting into lines 44 and 46, but it is to be recognized that depending on the type of separation being performed and the eventual destination of the component being separated, multiple lines may emanate from separations unit 42. In some embodiments, at least a portion of any water present in the alcoholic component may be removed in separations unit 42 before subsequent downstream processing takes place. In some embodiments, a phenolics liquid phase may be separated from the alcoholic component in separations unit 42 before further processing takes place, or the viscosity of the phenolics liquid phase may be reduced by at least partially depolymerizing the lignin therein (e.g., via thermal depolymerization). In some embodiments, a portion of the alcoholic component may be separated from the remainder of the liquid phase being processed in separations unit 42. Optionally, at least a portion of the separated alcoholic component may be recirculated to hydrothermal digestion unit 10 via recycle line 44, which is fluidly coupled to line 34, if desired.

The alcoholic component exiting separations unit 42 may be conveyed to reforming reactor 48 via line 46. In reforming reactor 48, a condensation reaction or other reforming reaction may take place. The reforming reaction taking place therein may be catalytic or non-catalytic. Although only one reforming reactor 48 has been depicted in FIG. 3, it is to be understood that any number of reforming reactors may be present. In reforming reactor 48, one or more further reforming reactions may take place, as described above. In some embodiments, a first reforming reaction may comprise a condensation reaction. Additional reforming reactions may comprise any combination of further catalytic reduction reactions (e.g., hydrogenation reactions, hydrogenolysis reactions, hydrotreating reactions, and the like), further condensation reactions, isomerization reactions, desulfurization reactions, dehydration reactions, oligomerization reactions, alkylation reactions, and the like. Such transformations may be used to convert the initially produced soluble carbohydrates into a biofuel. Such biofuels may include, for example, gasoline hydrocarbons, diesel fuels, jet fuels, and the like. As used herein, the term "gasoline hydrocarbons" refers to substances comprising predominantly $C_5$-$C_9$ hydrocarbons and having a boiling point of 32° C. to about 204° C. More generally, any fuel blend meeting the requirements of ASTM D2887 may be classified as a gasoline hydrocarbon. Suitable gasoline hydrocarbons may include, for example, straight run gasoline, naphtha, fluidized or thermally catalytically cracked gasoline, VB gasoline, and coker gasoline. As used herein, the term "diesel fuel" refers to substances comprising paraffinic hydrocarbons and having a boiling point ranging between about 187° C. and about 417° C., which is suitable for use in a compression ignition engine. More generally, any fuel blend meeting the requirements of ASTM D975 may also be defined as a diesel fuel. As used herein, the term "jet fuel" refers to substances meeting the requirements of ASTM D1655. In some embodiments, jet fuels may comprise a kerosene-type fuel having substantially $C_8$-$C_{16}$ hydrocarbons (Jet A and Jet A-1 fuels). In other embodiments, jet fuels may comprise a wide-cut or naphtha-type fuel having substantially $C_5$-$C_{15}$ hydrocarbons present therein (Jet B fuels).

Figure 4:
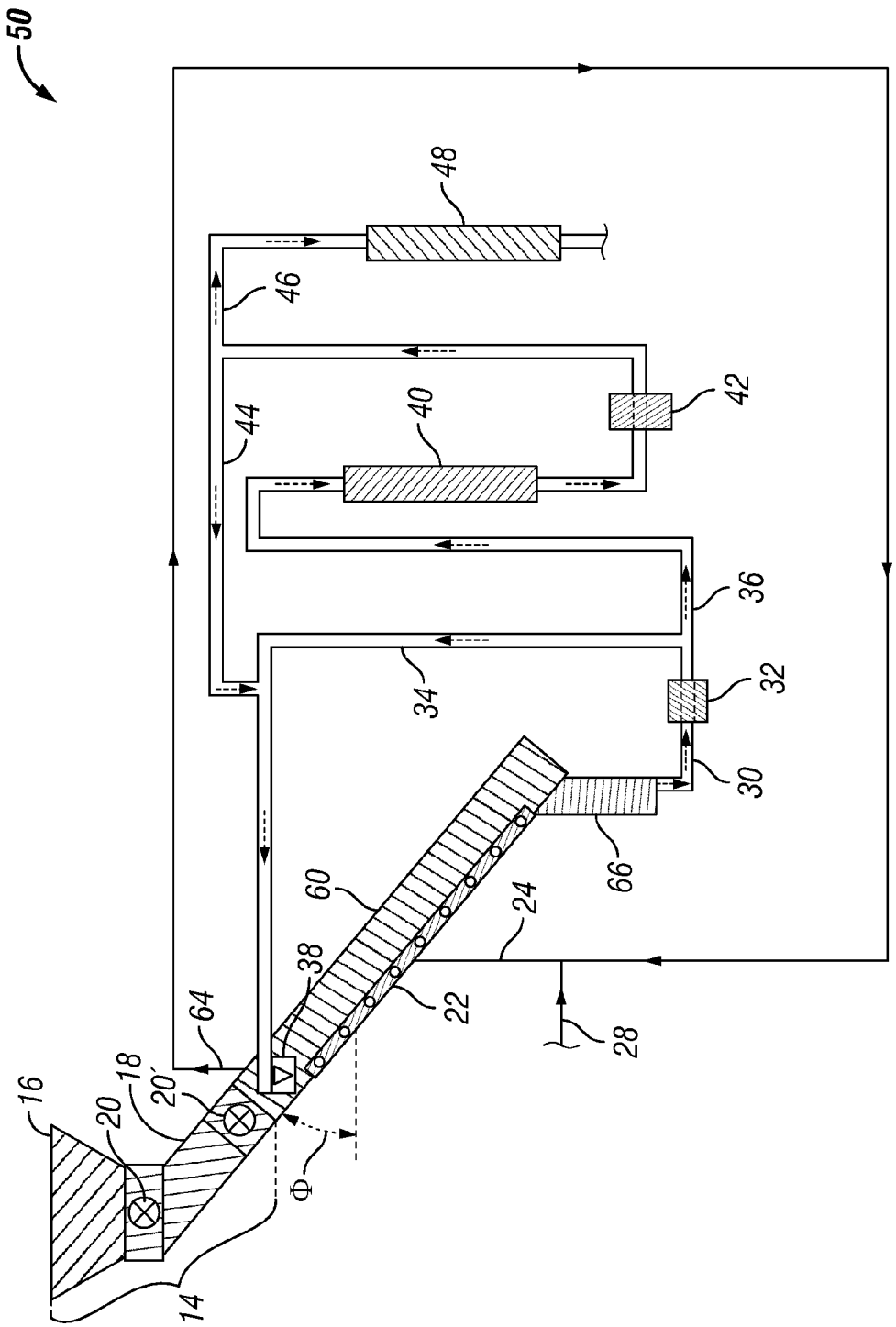
FIGS. 4 and 5 show schematics of illustrative biomass conversion systems containing an inclined digestion unit comprising a single-stage inclined tubular element.
Figure 5:
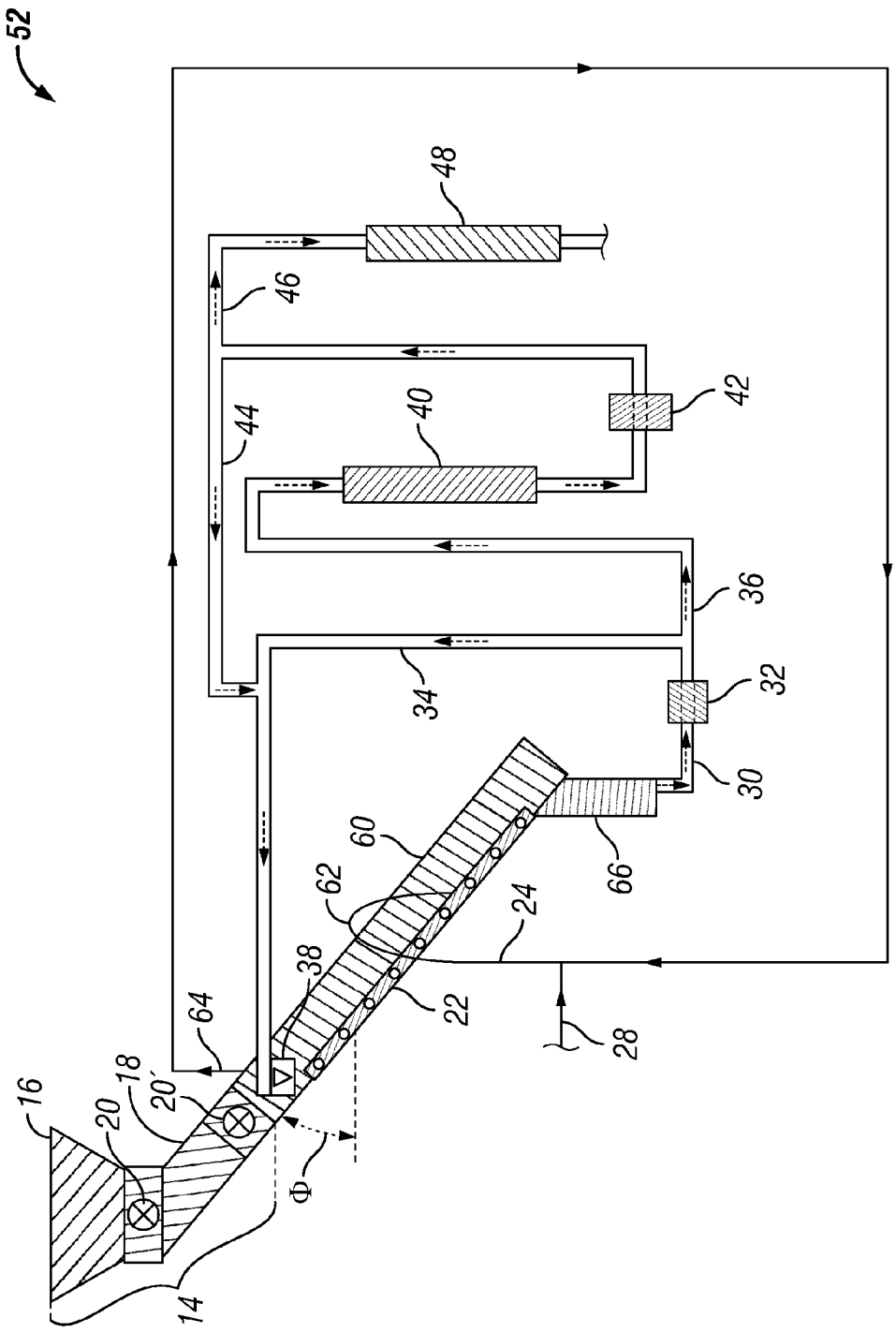

FIGS. 4 and 5 show schematics of illustrative biomass conversion systems 50 and 52 containing an inclined digestion unit comprising a single-stage inclined tubular element. As depicted in FIGS. 4 and 5, a hydrothermal digestion unit comprises inclined tubular element 60, which is inclined at angle Φ relative to horizontal. As discussed above, angle Φ may range from between about 5 degrees to about 85 degrees relative to horizontal, and the exemplary angle depicted in the figures should not be considered as limiting of the present disclosure.

Similar to the embodiment depicted in FIG. 3, solids introduction mechanism 14 may be operatively coupled to inclined tubular element 60. Again, solids introduction mechanism 14 may comprise loading mechanism 16 and pressure transition zone 18, but in the illustrative embodiments, depicted in FIGS. 4 and 5, pressure transition zone 18 has been tilted to generally match the angle of inclination of inclined tubular element 60. It should be recognized, however, that solids introduction mechanism 14 may remain in a generally vertical orientation as depicted in FIG. 3, with the operative coupling to inclined tubular element 60 being made longitudinally, rather than at its end as depicted in FIGS. 4 and 5. As in the embodiment depicted in FIG. 3, valves 20 and 20' are present and used for achieving pressure isolation during the addition of cellulosic biomass solids to inclined tubular element 60.

Longitudinally disposed along the lower surface of inclined tubular element 60 is gas distribution mechanism 22, around which or over which cellulosic biomass solids may pass as they descend through inclined tubular element 60. Gas distribution mechanism 22 may be located substantially parallel to the incline of inclined tubular element 60 in a locale therein where cellulosic biomass solids are present. Further description of the location of gas distribution mechanism 22 is provided hereinabove. Gas distribution mechanism 22 may be fluidly connected to gas distribution line 24. As depicted in FIG. 4, gas distribution line 24 may feed gas distribution mechanism 22 from its underside (i.e., below a fluid level of cellulosic biomass solids and fluid phase digestion medium contained in inclined tubular element 60). More desirably, as depicted in FIG. 5, gas distribution line 24 may feed gas distribution mechanism 22 from above via drop down feed 62.

Referring still to FIGS. 4 and 5, initial gas introduction or supplemental gas introduction may be made to gas distribution line 24 via line 28. In addition, biomass conversion systems 50 and 52 may be further configured such that a gas may be recycled within inclined tubular element 60. Specifically, gas recycle line 64 may be fluidly coupled to inclined tubular element 60 at a headspace where a gas may collect as the gas generally flows upward from gas distribution mechanism 22, and the gas may then be conveyed to gas distribution line 24, where it may be returned to inclined tubular element 60 via gas distribution mechanism 22.

Sump 66 is fluidly coupled to inclined tubular element 60 at its lowermost point, so that fluid phase digestion medium descending through inclined tubular element 60 or another fluid phase being formed during hydrothermal digestion may collect therein. For example, a phenolics liquid phase and slurry catalyst may also accumulate in sump 66. In addition, undigested cellulosic biomass solids, including cellulosic biomass fines, or non-digestible components of the cellulosic biomass solids may accumulate in sump 66. Fluidizable substances accumulated in sump 66 may be removed therefrom by fluid removal line 30. As described above in reference to FIG. 3, fluid removal line 30 may be fluidly coupled to separations unit 32, and a fluid exiting separations unit 32 may either be returned to inclined tubular element 60 via line 34 or conveyed forward via line 36 for further reforming. In some embodiments, a fluid phase digestion medium and slurry catalyst may be conveyed in line 34. In some or other embodiments, a phenolics liquid phase and slurry catalyst accumulated therein may be returned to inclined tubular element 60 in line 34. Again, although line 34 has been depicted as a single fluid conduit, it is to be recognized that multiple lines may be present if it is desired that different fluid phases are to be conveyed separately. A fluid being returned to inclined tubular element 60 via line 34 may be introduced thereto via flow distribution mechanism 38.

With continued reference to FIGS. 4 and 5, polishing reactor 40 may optionally be fluidly coupled to line 36, such that soluble carbohydrates in the fluid may be further formed into an alcoholic component and/or the degree of oxygenation of the alcoholic component may be further decreased. Thereafter, the alcoholic component may be conveyed to separations unit 42, where various further operations may take place prior to subsequent downstream processing, as described in more detail hereinabove. Optionally, at least a portion of a separated alcoholic component exiting separations unit 42 may be returned to inclined tubular element 60 via recycle line 44, which is fluidly coupled to line 34. The alcoholic component not being recirculated to inclined tubular element 60 may be conveyed to reforming reactor 48 via line 46. As discussed above, various further reforming reactions, including a condensation reaction, may take place in reforming reactor 48 and more than one reforming reactor 48 may be present.

Figure 6:
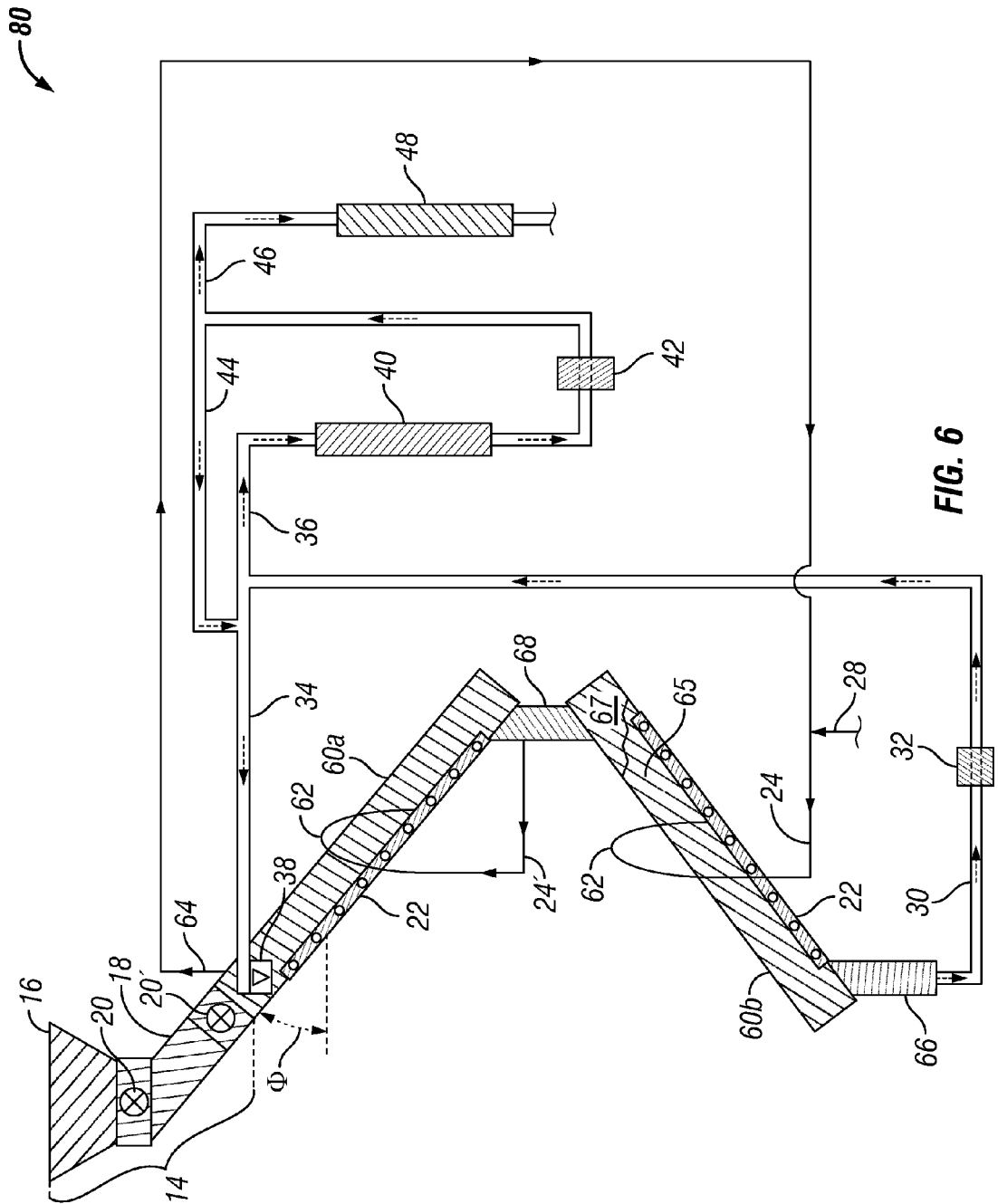
FIG. 6 shows a schematic of an illustrative biomass conversion system containing an inclined digestion unit comprising multiple inclined tubular elements that are fluidly coupled together in series.

FIG. 6 shows a schematic of illustrative biomass conversion system 80 containing an inclined digestion unit comprising multiple inclined tubular elements that are fluidly coupled together in series. Many of the elements depicted in FIG. 6 are substantially similar to those depicted in FIGS. 3-5 and described above. Accordingly, these elements will not be described again in detail. Unlike the embodiments depicted in FIGS. 4 and 5, the embodiment depicted in FIG. 6 contains upper inclined tubular element 60a that is fluidly coupled to lower inclined tubular element 60b via vertical fluid connection 68. As discussed above, vertical fluid connection 68 represents a convenient location from which a gas may be collected from inclined tubular element 60b and conveyed upward to inclined tubular element 60a. Accordingly, as depicted in FIG. 6, gas distribution line 24' may be fluidly connected to vertical fluid connection 68 to accomplish such gas withdrawal and recirculation. Although biomass conversion system 80 has been depicted in FIG. 6 as having only two inclined tubular elements 60a and 60b, it is to be recognized that any number of inclined tubular elements may be present and fluidly connected together in series. For example, there may be from between 2 and about 20 inclined tubular elements present and fluidly connected to one another via vertical fluid connection 68 in a manner similar to that depicted in FIG. 6.

In further regard to the methods described herein, the processing of cellulosic biomass solids to produce an alcoholic component will now be described in greater detail with reference to FIG. 6. Cellulosic biomass solids may be introduced from loading mechanism 16 to pressurization zone 18, where they may be elevated from atmospheric pressure to an elevated pressure that is present within inclined tubular elements 60a and 60b. Pressurization may take place using a gas or a liquid that is introduced to pressurization zone 18. After pressurization, valve 20' located between pressurization zone 18 and inclined tubular element 60a may be opened such that the cellulosic biomass solids drop via gravity into inclined tubular element 60a. As the cellulosic biomass solids enter inclined tubular element 60a, a fluid phase digestion medium and slurry catalyst may be admixed therewith via addition from line 34 and flow distribution mechanism 38.

After being admixed with the slurry catalyst and the fluid phase digestion medium, they may descend along the incline of inclined tubular element 60a as the coefficient of static friction is overcome. As the cellulosic biomass solids pass over or around gas distribution mechanism 22, molecular hydrogen may be introduced thereto and become distributed in the cellulosic biomass solids. Moreover, the upwardly directed flow of the molecular hydrogen may promote continued distribution of the slurry catalyst in the cellulosic biomass solids. Further discussion regarding the sourcing of molecular hydrogen for introduction to the cellulosic biomass solids follows below.

Once the cellulosic biomass solids, slurry catalyst, and fluid phase digestion medium have reached the lower portion of inclined tubular element 60a they may drop via gravity through vertical fluid connection 68 into inclined tubular element 60b. Once in inclined tubular element 60b, the cellulosic biomass solids may descend along its incline in a manner like that described above until they reach sump 66. Once reaching sump 66, the fluid phase digestion medium, any fluid phase formed from the cellulosic biomass solids (e.g., a phenolics liquid phase), and the slurry catalyst may accumulate therein. These components may be removed from sump 66 and processed further as described hereinafter.

Before further discussing processing of the components that have accumulated in sump 66, mention should be made of the desirability to control the introduction rate of the fluid phase digestion medium such that the amount thereof in inclined tubular elements 60a and 60b does not become excessive. Specifically, it may be desirable to control the introduction rate of the fluid phase digestion medium and the cellulosic biomass solids such that a liquid level in inclined tubular element 60b does not overfill its interior and enter vertical fluid connection 68. Accordingly, by controlling the introduction rate of fluid phase digestion medium to inclined tubular element 60a, a liquid level 65 in inclined tubular element 60b may be adjusted such that gas headspace 67 is maintained therein. Maintenance of gas headspace 67 may ensure that a continuous phase of introduced molecular hydrogen is present in vertical fluid connection 68. In this regard, it is to be noted that vertical fluid connection 68 differs from sump 66, since at least a portion of sump 66 contains a continuous liquid phase therein (i.e., the fluid phase digestion medium or another liquid phase). Accordingly, molecular hydrogen that has been introduced to inclined tubular element 60b may be removed at vertical fluid connection 68 with a low risk of removing a continuous liquid phase therefrom.

The sourcing and management of molecular hydrogen introduced to inclined tubular elements 60a and 60b will now be discussed. Once introduced molecular hydrogen has passed completely through a given portion of cellulosic biomass solids and formed a continuous gas phase thereabove, the molecular hydrogen may no longer be effective for stabilizing soluble carbohydrates via a catalytic reduction reaction. In order to make more effective use of the molecular hydrogen forming a continuous gas phase above the cellulosic biomass solids, the molecular hydrogen that has migrated upward through inclined tubular elements 60a and 60b may be withdrawn via gas recycle line 64. The molecular hydrogen in gas recycle line 64 may then be returned to inclined tubular element 60b via gas distribution line 24, which is fluidly connected to gas distribution mechanism 22 therein. Gas distribution line 24 may be fluidly connected to gas distribution mechanism 22 via drop down feed 62, such that the molecular hydrogen is introduced from above the cellulosic biomass solids. Although FIG. 6 has depicted molecular hydrogen from gas recirculation line 64 only being reintroduced to inclined tubular element 60b, it is to be recognized that gas recirculation line 64 may optionally be configured such that molecular hydrogen is reintroduced to both inclined tubular elements 60a and 60b. In addition, it may be more advantageous and economical in terms of molecular hydrogen management to supply the molecular hydrogen to inclined tubular element 60a from elsewhere, as discussed further below. Line 28 may be used to introduce startup molecular hydrogen to inclined tubular element 60b and/or to supplement the molecular hydrogen recirculating in inclined tubular elements 60a and 60b at a desired partial pressure.

Continuing with the discussion of molecular hydrogen sourcing and management with reference to FIG. 6, the molecular hydrogen in inclined tubular element 60b may proceed to gas headspace 67 and enter vertical fluid connection 68. Some of this molecular hydrogen may continue progressing upward through inclined tubular element 60a, above the cellulosic biomass solids contained therein, where it is eventually withdrawn via gas recycle line 64. Advantageously, a portion of the molecular hydrogen in vertical fluid connection 68 may be withdrawn via gas distribution line 24' and conveyed to gas distribution mechanism 22 within inclined tubular element 60a. The conveyed molecular hydrogen may then progress upward through the cellulosic biomass solids as they descend along inclined tubular element 60a, where it may continue to promote the stabilization of soluble carbohydrates, instead of ineffectively passing over the cellulosic biomass solids. The recirculation of molecular hydrogen in this manner can lessen the amount of molecular hydrogen needing to be supplied to biomass conversion system 80, since a given quantity of molecular hydrogen may be used to stabilize soluble carbohydrates in multiple locations within inclined tubular elements 60a and 60b. Although FIG. 6 has depicted molecular hydrogen as being withdrawn from vertical fluid connection 68, it may also be withdrawn from gas headspace 67, if desired.

The various components that have accumulated in sump 66 may be removed via line 30. Optionally, the components may be separated in separations unit 32, such as, for example, to separate the fluid phase digestion medium from a phenolics liquid phase. A separated fluid phase containing the slurry catalyst, which may comprise the fluid phase digestion medium, the phenolics liquid phase, or any combination thereof may be returned to inclined tubular element 60a via line 34, where these components may continue to be employed in the hydrothermal digestion process. The choice of whether to convey the phenolics liquid phase to inclined tubular element 60a may depend, at least in part, upon the amount of phenolics liquid phase that has formed, its viscosity, and/or the degree to which the slurry catalyst has accumulated in the phenolics liquid phase.

Fluid phase digestion medium and/or phenolics liquid phase not being returned to inclined tubular element 60a may be conveyed by line 36 and further processed as generally described hereinabove. Optionally, the alcoholic component contained in the fluid phase digestion medium may be further formed in polishing reactor 40 and/or the degree of oxygenation of the alcoholic component may be further decreased therein. Optionally thereafter, the alcoholic component may undergo further separation in separations unit 42, such as removing at least a portion of any water present from the fluid phase digestion medium prior to conveying the alcoholic component to reforming reactor 48. Further optionally, at least a portion of the alcoholic component may be returned to inclined tubular element 60a after separation. Particular benefits of returning a separated alcoholic component to inclined tubular element 60a may include, for example, maintaining a clean catalyst surface for better promoting the stabilization of soluble carbohydrates. Finally, the alcoholic component may undergo a condensation reaction or other reforming reaction in reforming reactor 48 in the process of being transformed into a biofuel.

As discussed above in reference to the drawings, the cellulosic biomass solids may be introduced to the hydrothermal digestion unit separately from the fluid phase digestion medium and the cellulosic biomass solids. However, in alternative embodiments, the fluid phase digestion medium and slurry catalyst may be recirculated to the cellulosic biomass solids such that the cellulosic biomass solids, the fluid phase digestion medium, and the slurry catalyst are all introduced to the hydrothermal digestion unit at substantially the same time. For example, in alternative embodiments to those depicted in the drawings, line 34 may be positioned to supply fluid phase digestion medium and slurry catalyst directly to cellulosic biomass solids contained in pressurization zone 18, instead of being directly returned to the hydrothermal digestion unit.

As further discussed above, methods described herein may further comprise removing at least a portion of the fluid phase digestion medium and the slurry catalyst from the hydrothermal digestion unit after they have descended the one or more inclined surfaces or inclined tubular elements. In some embodiments, the methods described herein may further comprise returning at least a portion of the fluid phase digestion medium and the slurry catalyst to the hydrothermal digestion unit. As discussed above, returning the fluid phase digestion medium and the slurry catalyst to the hydrothermal digestion unit may allow hydrothermal digestion to continue unabated and promote the downward migration of the cellulosic biomass solids via fluid motion in the hydrothermal digestion unit. In some embodiments, returning at least a portion of the fluid phase digestion medium and the slurry catalyst to the hydrothermal digestion unit may comprise conveying the fluid phase digestion medium and the slurry catalyst to an uppermost inclined surface or inclined tubular element when more than one inclined surface or inclined tubular element is present. In some embodiments, the fluid phase digestion medium and the slurry catalyst may be conveyed from a lowermost inclined surface or inclined tubular element, or a sump connected thereto, in which these components have accumulated. In embodiments in which only a single inclined surface or inclined tubular element is present in the hydrothermal digestion unit, the fluid phase digestion medium and slurry catalyst may be conveyed from a lowermost portion of the inclined surface or inclined tubular element, or a sump connected thereto, to an upper portion of the inclined surface or inclined tubular element (e.g., at a location where cellulosic biomass solids are being introduced thereto).

As further described above in reference to the drawings, the methods described herein may further comprise transferring molecular hydrogen from a lower inclined tubular element to an upper inclined tubular element. By transferring molecular hydrogen in this manner, the molecular hydrogen may become redistributed in cellulosic biomass solids descending through the upper inclined tubular element and promote the stabilization of soluble carbohydrates being produced therefrom, instead of inefficiently passing over the cellulosic biomass solids without being distributed therein, as would occur if molecular hydrogen transfer had not taken place. In some embodiments, the transfer of molecular hydrogen may take place from a lower inclined tubular element to an upper inclined tubular element, where the inclined tubular elements are vertically adjacent to one another. However, in other embodiments, molecular hydrogen transfer may take place between non-vertically adjacent inclined tubular elements, if desired.

In addition to the transfer of molecular hydrogen from a lower inclined tubular element to an upper inclined tubular element, the transfer of molecular hydrogen may take place in the opposite direction as well. That is, in some embodiments, molecular hydrogen may be transferred from an upper inclined tubular element to a lower inclined tubular element. In more specific embodiments, molecular hydrogen may be collected from an uppermost inclined tubular element and returned to a lower inclined tubular element, thereby allowing the returned molecular hydrogen to begin upward transit anew within the hydrothermal digestion unit. In still more specific embodiments, the molecular hydrogen may be transferred from an uppermost inclined tubular element to a lowermost inclined tubular element. However, in other embodiments, transfer of the molecular hydrogen to any inclined tubular element below the uppermost inclined tubular element may also be performed if desired.

Further discussion of the transformations that take place on the cellulosic biomass solids in the hydrothermal digestion unit and thereafter are now described in greater detail. In various embodiments, the alcoholic component derived from the cellulosic biomass solids may be formed by a catalytic reduction reaction of soluble carbohydrates, where the soluble carbohydrates are derived from the cellulosic biomass solids. As described above, the methods and systems set forth herein can help promote adequate distribution of the slurry catalyst and the molecular hydrogen throughout the cellulosic biomass solids such that the catalytic reduction reaction can more effectively take place.

In some embodiments, the catalytic reduction reaction used to produce the alcoholic component may take place at a temperature ranging between about 110° C. and about 300° C., or between about 170° C. and about 300° C., or between about 180° C. and about 290° C., or between about 150° C. and about 250° C. In some embodiments, the catalytic reduction reaction used to produce the alcoholic component may take place at a pH ranging between about 7 and about 13, or between about 10 and about 12. In other embodiments, the catalytic reduction reaction may take place under acidic conditions, such as at a pH of about 5 to about 7. Acids, bases, and buffers may be introduced as necessary to achieve a desired pH level. In some embodiments, the catalytic reduction reaction may be conducted under a hydrogen partial pressure ranging between about 1 bar (absolute) and about 150 bar, or between about 15 bar and about 140 bar, or between about 30 bar and about 130 bar, or between about 50 bar and about 110 bar.

In various embodiments, the fluid phase digestion medium in which the hydrothermal digestion and catalytic reduction reaction are conducted may comprise an organic solvent and water. Although any organic solvent that is at least partially miscible with water may be used as a digestion solvent, particularly advantageous organic solvents are those that can be directly converted into fuel blends and other materials without being separated from the alcoholic component being produced from the cellulosic biomass solids. That is, particularly advantageous organic solvents are those that may be co-processed along with the alcoholic component during downstream reforming reactions into fuel blends and other materials. Suitable organic solvents in this regard may include, for example, ethanol, ethylene glycol, propylene glycol, glycerol, and any combination thereof.

In some embodiments, the fluid phase digestion medium may further comprise a small amount of a monohydric alcohol. The presence of at least some monohydric alcohols in the fluid phase digestion medium may desirably enhance the hydrothermal digestion and/or the catalytic reduction reactions being conducted therein. For example, inclusion of about 1% to about 5% by weight monohydric alcohols in the fluid phase digestion medium may desirably maintain catalyst activity due to a surface cleaning effect. Monohydric alcohols present in the digestion solvent may arise from any source. In some embodiments, the monohydric alcohols may be formed via the in situ catalytic reduction reaction process being conducted therein. In some or other embodiments, the monohydric alcohols may be formed during further chemical transformations of the initially formed alcoholic component. In still other embodiments, the monohydric alcohols may be sourced from an external feed that is in flow communication with the cellulosic biomass solids.

In some embodiments, the fluid phase digestion medium may comprise between about 1% water and about 99% water. Although higher percentages of water may be more favorable from an environmental standpoint, higher quantities of organic solvent may more effectively promote hydrothermal digestion due to the organic solvent's greater propensity to solubilize carbohydrates and promote catalytic reduction of the soluble carbohydrates. In some embodiments, the fluid phase digestion medium may comprise about 90% or less water by weight. In other embodiments, the fluid phase digestion medium may comprise about 80% or less water by weight, or about 70% or less water by weight, or about 60% or less water by weight, or about 50% or less water by weight, or about 40% or less water by weight, or about 30% or less water by weight, or about 20% or less water by weight, or about 10% or less water by weight, or about 5% or less water by weight.

In some embodiments, catalysts capable of activating molecular hydrogen and conducting a catalytic reduction reaction may comprise a metal such as, for example, Cr, Mo, W, Re, Mn, Cu, Cd, Fe, Co, Ni, Pt, Pd, Rh, Ru, Ir, Os, and alloys or any combination thereof, either alone or with promoters such as Au, Ag, Cr, Zn, Mn, Sn, Bi, B, O, and alloys or any combination thereof. In some embodiments, the catalysts and promoters may allow for hydrogenation and hydrogenolysis reactions to occur at the same time or in succession of one another. In some embodiments, such catalysts may also comprise a carbonaceous pyropolymer catalyst containing transition metals (e.g., Cr, Mo, W, Re, Mn, Cu, and Cd) or Group VIII metals (e.g., Fe, Co, Ni, Pt, Pd, Rh, Ru, Ir, and Os). In some embodiments, the foregoing catalysts may be combined with an alkaline earth metal oxide or adhered to a catalytically active support. In some or other embodiments, the catalyst capable of activating molecular hydrogen may be deposited on a catalyst support that is not itself catalytically active.

In some embodiments, the catalyst that is capable of activating molecular hydrogen may comprise a slurry catalyst. In some embodiments, the slurry catalyst may comprise a poison-tolerant catalyst. As used herein the term "poison-tolerant catalyst" refers to a catalyst that is capable of activating molecular hydrogen without needing to be regenerated or replaced due to low catalytic activity for at least about 12 hours of continuous operation. Use of a poison-tolerant catalyst may be particularly desirable when reacting soluble carbohydrates derived from cellulosic biomass solids that have not had catalyst poisons removed therefrom. Catalysts that are not poison tolerant may also be used to achieve a similar result, but they may need to be regenerated or replaced more frequently than does a poison-tolerant catalyst.

In some embodiments, suitable poison-tolerant catalysts may include, for example, sulfided catalysts. In some or other embodiments, nitrided catalysts may be used as poison-tolerant catalysts. Sulfided catalysts suitable for activating molecular hydrogen are described in commonly owned US20120317872 and US20130109896, each of which is incorporated herein by reference in its entirety. Sulfiding may take place by treating the catalyst with hydrogen sulfide or an alternative sulfiding agent, optionally while the catalyst is disposed on a solid support. In more particular embodiments, the poison-tolerant catalyst may comprise a sulfided cobalt-molybdate catalyst, such as a catalyst comprising about 1-10 wt. % cobalt oxide and up to about 30 wt. % molybdenum trioxide. In other embodiments, catalysts containing Pt or Pd may also be effective poison-tolerant catalysts for use in the techniques described herein. When mediating in situ catalytic reduction reaction processes, sulfided catalysts may be particularly well suited to form reaction products comprising a substantial fraction of glycols (e.g., $C_2$-$C_6$ glycols) without producing excessive amounts of the corresponding monohydric alcohols. Although poison-tolerant catalysts, particularly sulfided catalysts, may be well suited for forming glycols from soluble carbohydrates, it is to be recognized that other types of catalysts, which may not necessarily be poison-tolerant, may also be used to achieve a like result in alternative embodiments. As will be recognized by one having ordinary skill in the art, various reaction parameters (e.g., temperature, pressure, catalyst composition, introduction of other components, and the like) may be modified to favor the formation of a desired reaction product. Given the benefit of the present disclosure, one having ordinary skill in the art will be able to alter various reaction parameters to change the product distribution obtained from a particular catalyst and set of reactants.

In some embodiments, slurry catalysts suitable for use in the methods described herein may be sulfided by dispersing a slurry catalyst in a fluid phase and adding a sulfiding agent thereto. Suitable sulfiding agents may include, for example, organic sulfoxides (e.g., dimethyl sulfoxide), hydrogen sulfide, salts of hydrogen sulfide (e.g., NaSH), and the like. In some embodiments, the slurry catalyst may be concentrated in the fluid phase after sulfiding, and the concentrated slurry may then be distributed in the cellulosic biomass solids using fluid flow. Illustrative techniques for catalyst sulfiding that may be used in conjunction with the methods described herein are described in U.S. Patent Application Publication No. 20100236988 and incorporated herein by reference in its entirety.

In various embodiments, slurry catalysts used in conjunction with the methods described herein may have a particulate size of about 250 microns or less. In some embodiments, the slurry catalyst may have a particulate size of about 100 microns or less, or about 10 microns or less. In some embodiments, the minimum particulate size of the slurry catalyst may be about 1 micron. In some embodiments, the slurry catalyst may comprise catalyst fines in the processes described herein. As used herein, the term "catalyst fines" refers to solid catalysts having a nominal particulate size of about 100 microns or less. Catalyst fines may be generated from catalyst production processes, for example, during extrusion of solid catalysts. Catalyst fines may also be produced by grinding larger catalyst solids or during regeneration of catalyst solids. Suitable methods for producing catalyst fines are described in U.S. Pat. Nos. 6,030,915 and 6,127,299, each of which is incorporated herein by reference in its entirety. In some instances, catalyst fines may be intentionally removed from a solid catalyst production run, since they may be difficult to sequester in some catalytic processes. Techniques for removing catalyst fines from larger catalyst solids may include, for example, sieving or like size separation processes. When conducting in situ catalytic reduction reaction processes, such as those described herein, catalyst fines may be particularly well suited, since they can be easily fluidized and distributed in the interstitial pore space of the digesting cellulosic biomass solids.

Catalysts that are not particularly poison-tolerant may also be used in conjunction with the techniques described herein. Such catalysts may include, for example, Ru, Pt, Pd, or compounds thereof disposed on a solid support such as, for example, Ru on titanium dioxide or Ru on carbon. Although such catalysts may not have particular poison tolerance, they may be regenerable, such as through exposure of the catalyst to water at elevated temperatures, which may be in either a subcritical state or a supercritical state.

In some embodiments, the catalysts used in conjunction with the processes described herein may be operable to generate molecular hydrogen. For example, in some embodiments, catalysts suitable for aqueous phase reforming (i.e., APR catalysts) may be used. Suitable APR catalysts may include, for example, catalysts comprising Pt, Pd, Ru, Ni, Co, or other Group VIII metals alloyed or modified with Re, Mo, Sn, or other metals.

In some embodiments, the alcoholic component formed from the cellulosic biomass solids may be further reformed into a biofuel. Reforming the alcoholic component into a biofuel or other material may comprise any combination and sequence of further hydrogenolysis reactions and/or hydrogenation reactions, condensation reactions, isomerization reactions, oligomerization reactions, hydrotreating reactions, alkylation reactions, dehydration reactions, desulfurization reactions, and the like. The subsequent reforming reactions may be catalytic or non-catalytic. In some embodiments, an initial operation of downstream reforming may comprise a condensation reaction, often conducted in the presence of a condensation catalyst, in which the alcoholic component or a product derived therefrom is condensed with another molecule to form a higher molecular weight compound. As used herein, the term "condensation reaction" will refer to a chemical transformation in which two or more molecules are coupled with one another to form a carbon-carbon bond in a higher molecular weight compound, usually accompanied by the loss of a small molecule such as water or an alcohol. An illustrative condensation reaction is the Aldol condensation reaction, which will be familiar to one having ordinary skill in the art. Additional disclosure regarding condensation reactions and catalysts suitable for promoting condensation reactions is provided hereinbelow.

In some embodiments, methods described herein may further comprise performing a condensation reaction on the alcoholic component or a product derived therefrom. In various embodiments, the condensation reaction may take place at a temperature ranging between about 5° C. and about 500° C. The condensation reaction may take place in a condensed phase (e.g., a liquor phase) or in a vapor phase. For condensation reactions taking place in a vapor phase, the temperature may range between about 75° C. and about 500° C., or between about 125° C. and about 450° C. For condensation reactions taking place in a condensed phase, the temperature may range between about 5° C. and about 475° C., or between about 15° C. and about 300° C., or between about 20° C. and about 250° C.

In various embodiments, the higher molecular weight compound produced by the condensation reaction may comprise $\geq C_4$ hydrocarbons. In some or other embodiments, the higher molecular weight compound produced by the condensation reaction may comprise $\geq C_6$ hydrocarbons. In some embodiments, the higher molecular weight compound produced by the condensation reaction may comprise $C_4$-$C_{30}$ hydrocarbons. In some embodiments, the higher molecular weight compound produced by the condensation reaction may comprise $C_6$-$C_{30}$ hydrocarbons. In still other embodiments, the higher molecular weight compound produced by the condensation reaction may comprise $C_4$-$C_{24}$ hydrocarbons, or $C_6$-$C_{24}$ hydrocarbons, or $C_4$-$C_{18}$ hydrocarbons, or $C_6$-$C_{18}$ hydrocarbons, or $C_4$-$C_{12}$ hydrocarbons, or $C_6$-$C_{12}$ hydrocarbons. As used herein, the term "hydrocarbons" refers to compounds containing both carbon and hydrogen without reference to other elements that may be present. Thus, heteroatom-substituted compounds are also described herein by the term "hydrocarbons."

The particular composition of the higher molecular weight compound produced by the condensation reaction may vary depending on the catalyst(s) and temperatures used for both the catalytic reduction reaction and the condensation reaction, as well as other parameters such as pressure. For example, in some embodiments, the product of the condensation reaction may comprise $\geq C_4$ alcohols and/or ketones that are produced concurrently with or in lieu of $\geq C_4$ hydrocarbons. In some embodiments, the $\geq C_4$ hydrocarbons produced by the condensation reaction may contain various olefins in addition to alkanes of various sizes, typically branched alkanes. In still other embodiments, the $\geq C_4$ hydrocarbons produced by the condensation reaction may also comprise cyclic hydrocarbons and/or aromatic compounds. In some embodiments, the higher molecular weight compound produced by the condensation reaction may be further subjected to a catalytic reduction reaction to transform a carbonyl functionality therein to an alcohol and/or a hydrocarbon and to convert olefins into alkanes.

Exemplary compounds that may be produced by a condensation reaction include, for example, $\geq C_4$ alkanes, $\geq C_4$ alkenes, $\geq C_5$ cycloalkanes, $\geq C_5$ cycloalkenes, aryls, fused aryls, $\geq C_4$ alcohols, $\geq C_4$ ketones, and mixtures thereof. The $\geq C_4$ alkanes and $\geq C_4$ alkenes may range from 4 to about 30 carbon atoms (i.e. $C_4$-$C_{30}$ alkanes and $C_4$-$C_{30}$ alkenes) and may be branched or straight chain alkanes or alkenes. The $\geq C_4$ alkanes and $\geq C_4$ alkenes may also include fractions of $C_7$-$C_{14}$, $C_{12}$-$C_{24}$ alkanes and alkenes, respectively, with the $C_7$-$C_{14}$ fraction directed to jet fuel blends, and the $C_{12}$-$C_{24}$ fraction directed to diesel fuel blends and other industrial applications. Examples of various $\geq C_4$ alkanes and $\geq C_4$ alkenes that may be produced by the condensation reaction include, without limitation, butane, butene, pentane, pentene, 2-methylbutane, hexane, hexene, 2-methylpentane, 3-methylpentane, 2,2-dimethylbutane, 2,3-dimethylbutane, heptane, heptene, octane, octene, 2,2,4,-trimethylpentane, 2,3-dimethylhexane, 2,3,4-trimethylpentane, 2,3-dimethylpentane, nonane, nonene, decane, decene, undecane, undecene, dodecane, dodecene, tridecane, tridecene, tetradecane, tetradecene, pentadecane, pentadecene, hexadecane, hexadecene, heptyldecane, heptyldecene, octyldecane, octyldecene, nonyldecane, nonyldecene, eicosane, eicosene, uneicosane, uneicosene, doeicosane, doeicosene, trieicosane, trieicosene, tetraeicosane, tetraeicosene, and isomers thereof.

The $\geq C_5$ cycloalkanes and $\geq C_5$ cycloalkenes may have from 5 to about 30 carbon atoms and may be unsubstituted, mono-substituted or multi-substituted. In the case of mono-substituted and multi-substituted compounds, the substituted group may include a branched $\geq C_3$ alkyl, a straight chain $\geq C_1$ alkyl, a branched $\geq C_3$ alkylene, a straight chain $\geq C_1$ alkylene, a straight chain $\geq C_2$ alkylene, an aryl group, or a combination thereof. In some embodiments, at least one of the substituted groups may include a branched $C_3$-$C_{12}$ alkyl, a straight chain $C_1$-$C_{12}$ alkyl, a branched $C_3$-$C_{12}$ alkylene, a straight chain $C_1$-$C_{12}$ alkylene, a straight chain $C_2$-$C_{12}$ alkylene, an aryl group, or a combination thereof. In yet other embodiments, at least one of the substituted groups may include a branched $C_3$-$C_4$ alkyl, a straight chain $C_1$-$C_4$ alkyl, a branched $C_3$-$C_4$ alkylene, a straight chain $C_1$-$C_4$ alkylene, a straight chain $C_2$-$C_4$ alkylene, an aryl group, or any combination thereof. Examples of $\geq C_5$ cycloalkanes and $\geq C_5$ cycloalkenes that may be produced by the condensation reaction include, without limitation, cyclopentane, cyclopentene, cyclohexane, cyclohexene, methylcyclopentane, methylcyclopentene, ethylcyclopentane, ethylcyclopentene, ethylcyclohexane, ethylcyclohexene, and isomers thereof.

The moderate fractions of the condensation reaction, such as $C_7$-$C_{14}$, may be separated for jet fuel, while heavier fractions, such as $C_{12}$-$C_{24}$, may be separated for diesel use. The heaviest fractions may be used as lubricants or cracked to produce additional gasoline and/or diesel fractions. The $\geq C_4$ compounds may also find use as industrial chemicals, whether as an intermediate or an end product. For example, the aryl compounds toluene, xylene, ethylbenzene, para-xylene, meta-xylene, and ortho-xylene may find use as chemical intermediates for the production of plastics and other products. Meanwhile, $C_9$ aromatic compounds and fused aryl compounds, such as naphthalene, anthracene, tetrahydronaphthalene, and decahydronaphthalene, may find use as solvents or additives in industrial processes.

In some embodiments, a single catalyst may mediate the transformation of the alcoholic component into a form suitable for undergoing a condensation reaction as well as mediating the condensation reaction itself. In other embodiments, a first catalyst may be used to mediate the transformation of the alcoholic component into a form suitable for undergoing a condensation reaction, and a second catalyst may be used to mediate the condensation reaction. Unless otherwise specified, it is to be understood that reference herein to a condensation reaction and condensation catalyst refers to either type of condensation process. Further disclosure of suitable condensation catalysts now follows.

In some embodiments, a single catalyst may be used to form a higher molecular weight compound via a condensation reaction. Without being bound by any theory or mechanism, it is believed that such catalysts may mediate an initial dehydrogenation of the alcoholic component, followed by a condensation reaction of the dehydrogenated alcoholic component. Zeolite catalysts are one type of catalyst suitable for directly converting alcohols to condensation products in such a manner. A particularly suitable zeolite catalyst in this regard may be ZSM-5, although other zeolite catalysts may also be suitable.

In some embodiments, two catalysts may be used to form a higher molecular weight compound via a condensation reaction. Without being bound by any theory or mechanism, it is believed that the first catalyst may mediate an initial dehydrogenation of the alcoholic component, and the second catalyst may mediate a condensation reaction of the dehydrogenated alcoholic component. Like the single-catalyst embodiments discussed previously above, in some embodiments, zeolite catalysts may be used as either the first catalyst or the second catalyst. Again, a particularly suitable zeolite catalyst in this regard may be ZSM-5, although other zeolite catalysts may also be suitable.

Various catalytic processes may be used to form higher molecular weight compounds by a condensation reaction. In some embodiments, the catalyst used for mediating a condensation reaction may comprise a basic site, or both an acidic site and a basic site. Catalysts comprising both an acidic site and a basic site will be referred to herein as multi-functional catalysts. In some or other embodiments, a catalyst used for mediating a condensation reaction may comprise one or more metal atoms. Any of the condensation catalysts may also optionally be disposed on a solid support, if desired.

In some embodiments, the condensation catalyst may comprise a basic catalyst comprising Li, Na, K, Cs, B, Rb, Mg, Ca, Sr, Si, Ba, Al, Zn, Ce, La, Y, Sc, Y, Zr, Ti, hydrotalcite, zinc-aluminate, phosphate, base-treated aluminosilicate zeolite, a basic resin, basic nitride, alloys or any combination thereof. In some embodiments, the basic catalyst may also comprise an oxide of Ti, Zr, V, Nb, Ta, Mo, Cr, W, Mn, Re, Al, Ga, In, Co, Ni, Si, Cu, Zn, Sn, Cd, Mg, P, Fe, or any combination thereof. In some embodiments, the basic catalyst may comprise a mixed-oxide basic catalyst. Suitable mixed-oxide basic catalysts may comprise, for example, Si—Mg—O, Mg—Ti—O, Y—Mg—O, Y—Zr—O, Ti—Zr—O, Ce—Zr—O, Ce—Mg—O, Ca—Zr—O, La—Zr—O, B—Zr—O, La—Ti—O, B—Ti—O, and any combination thereof. In some embodiments, the condensation catalyst may further include a metal or alloys comprising metals such as, for example, Cu, Ag, Au, Pt, Ni, Fe, Co, Ru, Zn, Cd, Ga, In, Rh, Pd, Ir, Re, Mn, Cr, Mo, W, Sn, Bi, Pb, Os, alloys and combinations thereof. Use of metals in the condensation catalyst may be desirable when a dehydrogenation reaction is to be carried out in concert with the condensation reaction. Basic resins may include resins that exhibit basic functionality. The basic catalyst may be self-supporting or adhered to a support containing a material such as, for example, carbon, silica, alumina, zirconia, titania, vanadia, ceria, nitride, boron nitride, a heteropolyacid, alloys and mixtures thereof.

In some embodiments, the condensation catalyst may comprise a hydrotalcite material derived from a combination of MgO and $Al_2O_3$. In some embodiments, the condensation catalyst may comprise a zinc aluminate spinel formed from a combination of ZnO and $Al_2O_3$. In still other embodiments, the condensation catalyst may comprise a combination of ZnO, $Al_2O_3$, and CuO. Each of these materials may also contain an additional metal or alloy, including those more generally referenced above for basic condensation catalysts. In more particular embodiments, the additional metal or alloy may comprise a Group 10 metal such Pd, Pt, or any combination thereof.

In some embodiments, the condensation catalyst may comprise a basic catalyst comprising a metal oxide containing, for example, Cu, Ni, Zn, V, Zr, or any mixture thereof. In some or other embodiments, the condensation catalyst may comprise a zinc aluminate containing, for example, Pt, Pd, Cu, Ni, or any mixture thereof.

In some embodiments, the condensation catalyst may comprise a multi-functional catalyst having both an acidic functionality and a basic functionality. Such condensation catalysts may comprise a hydrotalcite, a zinc-aluminate, a phosphate, Li, Na, K, Cs, B, Rb, Mg, Si, Ca, Sr, Ba, Al, Ce, La, Sc, Y, Zr, Ti, Zn, Cr, or any combination thereof. In further embodiments, the multi-functional catalyst may also include one or more oxides from the group of Ti, Zr, V, Nb, Ta, Mo, Cr, W, Mn, Re, Al, Ga, In, Fe, Co, Ir, Ni, Si, Cu, Zn, Sn, Cd, P, and any combination thereof. In some embodiments, the multi-functional catalyst may include a metal such as, for example, Cu, Ag, Au, Pt, Ni, Fe, Co, Ru, Zn, Cd, Ga, In, Rh, Pd, Ir, Re, Mn, Cr, Mo, W, Sn, Os, alloys or combinations thereof. The basic catalyst may be self-supporting or adhered to a support containing a material such as, for example, carbon, silica, alumina, zirconia, titania, vanadia, ceria, nitride, boron nitride, a heteropolyacid, alloys and mixtures thereof.

In some embodiments, the condensation catalyst may comprise a metal oxide containing Pd, Pt, Cu or Ni. In still other embodiments, the condensation catalyst may comprise an aluminate or a zirconium metal oxide containing Mg and Cu, Pt, Pd or Ni. In still other embodiments, a multi-functional catalyst may comprise a hydroxyapatite (HAP) combined with one or more of the above metals.

In some embodiments, the condensation catalyst may also include a zeolite and other microporous supports that contain Group IA compounds, such as Li, Na, K, Cs and Rb. Preferably, the Group IA material may be present in an amount less than that required to neutralize the acidic nature of the support. A metal function may also be provided by the addition of group VIIIB metals, or Cu, Ga, In, Zn or Sn. In some embodiments, the condensation catalyst may be derived from the combination of MgO and $Al_2O_3$ to form a hydrotalcite material. Another condensation catalyst may comprise a combination of MgO and $ZrO_2$, or a combination of ZnO and $Al_2O_3$. Each of these materials may also contain an additional metal function provided by copper or a Group VIIIB metal, such as Ni, Pd, Pt, or combinations of the foregoing.

The condensation reaction mediated by the condensation catalyst may be carried out in any reactor of suitable design, including continuous-flow, batch, semi-batch or multi-system reactors, without limitation as to design, size, geometry, flow rates, and the like. The reactor system may also use a fluidized catalytic bed system, a swing bed system, fixed bed system, a moving bed system, or a combination of the above. In some embodiments, bi-phasic (e.g., liquid-liquid) and tri-phasic (e.g., liquid-liquid-solid) reactors may be used to carry out the condensation reaction.

In some embodiments, an acid catalyst may be used to optionally dehydrate at least a portion of the reaction product. Suitable acid catalysts for use in the dehydration reaction may include, but are not limited to, mineral acids (e.g., HCl, $H_2SO_4$), solid acids (e.g., zeolites, ion-exchange resins) and acid salts (e.g., $LaCl_3$). Additional acid catalysts may include, without limitation, zeolites, carbides, nitrides, zirconia, alumina, silica, aluminosilicates, phosphates, titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and any combination thereof. In some embodiments, the dehydration catalyst may also include a modifier. Suitable modifiers may include, for example, La, Y, Sc, P, B, Bi, Li, Na, K, Rb, Cs, Mg, Ca, Sr, Ba, and any combination thereof. The modifiers may be useful, inter alia, to carry out a concerted hydrogenation/dehydrogenation reaction with the dehydration reaction. In some embodiments, the dehydration catalyst may also include a metal. Suitable metals may include, for example, Cu, Ag, Au, Pt, Ni, Fe, Co, Ru, Zn, Cd, Ga, In, Rh, Pd, Ir, Re, Mn, Cr, Mo, W, Sn, Os, alloys, and any combination thereof. The dehydration catalyst may be self supporting, supported on an inert support or resin, or it may be dissolved in a fluid.

Various operations may optionally be performed on the alcoholic component prior to conducting a condensation reaction. In addition, various operations may optionally be performed on a fluid phase containing the alcoholic component, thereby further transforming the alcoholic component or placing the alcoholic component in a form more suitable for taking part in a condensation reaction. These optional operations are now described in more detail below.

As described above, one or more liquid phases may be present when digesting cellulosic biomass solids. Particularly when cellulosic biomass solids are fed continuously or semi-continuously to the hydrothermal digestion unit, digestion of the cellulosic biomass solids may produce multiple liquid phases in the hydrothermal digestion unit. The liquid phases may be immiscible with one another, or they may be at least partially miscible with one another. In some embodiments, the one or more liquid phases may comprise a phenolics liquid phase comprising lignin or a product formed therefrom, an aqueous phase comprising the alcoholic component, a light organics phase, or any combination thereof. The alcoholic component being produced from the cellulosic biomass solids may be partitioned between the one or more liquid phases, or the alcoholic component may be located substantially in a single liquid phase. For example, the alcoholic component being produced from the cellulosic biomass solids may be located predominantly in an aqueous phase (e.g., an aqueous phase digestion solvent), although minor amounts of the alcoholic component may be partitioned to the phenolics liquid phase or a light organics phase. In various embodiments, the slurry catalyst may accumulate in the phenolics liquid phase as it forms, thereby complicating the return of the slurry catalyst to the cellulosic biomass solids in the manner described above. Alternative configurations for distributing slurry catalyst particulates in the cellulosic biomass solids when excessive catalyst accumulation in the phenolics liquid phase has occurred are described hereinafter.

Accumulation of the slurry catalyst in the phenolics liquid phase may, in some embodiments, be addressed by conveying this phase and the accumulated slurry catalyst therein to the same location where a fluid phase digestion medium is being contacted with cellulosic biomass solids. The fluid phase digestion medium and the phenolics liquid phase may be conveyed to the cellulosic biomass solids together or separately. Thusly, either the fluid phase digestion medium and/or the phenolics liquid phase may motively return the slurry catalyst back to the cellulosic biomass solids such that continued stabilization of soluble carbohydrates may take place. In some embodiments, at least a portion of the lignin in the phenolics liquid phase may be depolymerized before or while conveying the phenolics liquid phase for redistribution of the slurry catalyst. At least partial depolymerization of the lignin in the phenolics liquid phase may reduce the viscosity of this phase and make it easier to convey. Lignin depolymerization may take place chemically by hydrolyzing the lignin (e.g., with a base) or thermally by heating the lignin to a temperature of at least about 250° C. in the presence of molecular hydrogen and the slurry catalyst. Further details regarding lignin depolymerization and the use of viscosity monitoring as a means of process control are described in commonly owned U.S. Patent Application 61/720765, filed Oct. 31, 2012 and incorporated herein by reference in its entirety.

After forming the alcoholic component from the cellulosic biomass solids, at least a portion of the alcoholic component may be separated from the cellulosic biomass solids and further processed by performing a condensation reaction thereon, as generally described above. Processing of the alcoholic component that has partitioned between various liquid phases may take place with the phases separated from one another, or with the liquid phases mixed together. For example, in some embodiments, the alcoholic component in a fluid phase digestion medium may be processed separately from a light organics phase. In other embodiments, the light organics phase may be processed concurrently with the fluid phase digestion medium.

Optionally, the fluid phase digestion medium containing the alcoholic component may be subjected to a second catalytic reduction reaction external to the cellulosic biomass solids, if needed, for example, to increase the amount of soluble carbohydrates that are converted into the alcoholic component and/or to further reduce the degree of oxygenation of the alcoholic components that are formed. For example, in some embodiments, a glycol or more highly oxygenated alcohol may be transformed into a monohydric alcohol by performing a second catalytic reduction reaction. The choice of whether to perform a condensation reaction on a monohydric alcohol or a glycol may be based on a number of factors, as discussed in more detail below, and each approach may present particular advantages.

In some embodiments, a glycol produced from the cellulosic biomass solids may be fed to the condensation catalyst. Although glycols may be prone to coking when used in conjunction with condensation catalysts, particularly zeolite catalysts, the present inventors found the degree of coking to be manageable in the production of higher molecular weight compounds. Approaches for producing glycols from cellulosic biomass solids and feeding the glycols to a condensation catalyst are described in commonly owned U.S. Patent Application 61/720704, filed Oct. 31, 2012 and incorporated herein by reference in its entirety. A primary advantage of feeding glycols to a condensation catalyst is that removal of water from glycols is considerably easier than from monohydric alcohols. Excessive water exposure can be particularly detrimental for zeolite catalysts and shorten their lifetime. Although monohydric alcohols are typically a preferred substrate for zeolite catalysts, they may be difficult to prepare in dried form due to azeotrope formation with water. Glycols, in contrast, are not believed to readily form binary azeotropes with water and may be produced in dried form by distillation.

In some embodiments, a dried alcoholic component, particularly a dried glycol, may be produced from cellulosic biomass solids and fed to a condensation catalyst. As used herein, the term "dried alcoholic component" refers to a fluid phase containing an alcoholic component that has had a least a portion of the water removed therefrom. Likewise, the terms "dried glycol" and "dried monohydric alcohol" respectively refer to a glycol or a monohydric alcohol that has had at least a portion of the water removed therefrom. It is to be recognized that a dried alcoholic component need not necessarily be completely anhydrous when dried, simply that its water content be reduced (e.g., less than 50 wt. % water). In some embodiments, the dried alcoholic component may comprise about 40 wt. % or less water. In some or other embodiments, the dried alcoholic component may comprise about 35 wt. % or less water, or about 30 wt. % or less water, or about 25 wt. % or less water, or about 20 wt. % or less water, or about 15 wt. % or less water, or about 10 wt. % or less water, or about 5 wt. % or less water. In some embodiments of the methods described herein, a substantially anhydrous alcoholic component may be produced upon drying. As used herein, a substance will be considered to be substantially anhydrous if it contains about 5 wt. % water or less.

In other embodiments, it may be more desirable to feed monohydric alcohols to the condensation catalyst due to a lower incidence of coking. As previously described, monohydric alcohols may be more difficult to produce in dried form due to azeotrope formation during distillation. In some embodiments, monohydric alcohols produced from cellulosic biomass solids may be fed directly to a condensation catalyst, without drying. In other embodiments, dried monohydric alcohols may be fed to a condensation catalyst. In some embodiments, dried monohydric alcohols may be produced from dried glycols. Specifically, dried glycols may be produced as described hereinabove, and the dried glycols may then be subjected to a catalytic reduction reaction to produce monohydric alcohols. The monohydric alcohols may contain a comparable amount of water to that present in the dried glycols from which they were formed. Thus, forming dried monohydric alcohols in the foregoing manner may desirably allow a reduced incidence of coking to be realized while maintaining lifetime of the condensation catalyst by providing a dried feed. The foregoing approach for producing dried monohydric alcohols from cellulosic biomass solids is described in commonly owned U.S. Patent Application 61/720714, filed Oct. 31, 2012 and incorporated herein by reference in its entirety.

In some embodiments, a phenolics liquid phase formed from the cellulosic biomass solids may be further processed. Processing of the phenolics liquid phase may facilitate the catalytic reduction reaction being performed to stabilize soluble carbohydrates. In addition, further processing of the phenolics liquid phase may be coupled with the production of dried glycols or dried monohydric alcohols for feeding to a condensation catalyst. Moreover, further processing of the phenolics liquid phase may produce methanol and phenolic compounds from degradation of the lignin present in the cellulosic biomass solids, thereby increasing the overall weight percentage of the cellulosic biomass solids that may be transformed into useful materials. Finally, further processing of the phenolics liquid phase may improve the lifetime of the slurry catalyst.

Various techniques for processing a phenolics liquid phase produced from cellulosic biomass solids are described in commonly owned U.S. Patent Applications 61/720689, 61/720747, and 61/720774, each filed on Oct. 31, 2012 and incorporated herein by reference in its entirety. As described therein, in some embodiments, the viscosity of the phenolics liquid phase may be reduced in order to facilitate conveyance or handling of the phenolics liquid phase. As further described therein, deviscosification of the phenolics liquid phase may take place by chemically hydrolyzing the lignin and/or heating the phenolics liquid phase in the presence of molecular hydrogen (i.e., hydrotreating) to depolymerize at least a portion of the lignin present therein in the presence of accumulated slurry catalyst. Deviscosification of the phenolics liquid phase may take place before or after separation of the phenolics liquid phase from one or more of the other liquid phases present, and thermal deviscosification may be coupled to the reaction or series of reactions used to produce the alcoholic component from the cellulosic biomass solids. Moreover, after deviscosification of the phenolics liquid phase, the slurry catalyst may be removed therefrom. The catalyst may then be regenerated, returned to the cellulosic biomass solids, or any combination thereof.

In some embodiments, heating of the cellulosic biomass solids and the fluid phase digestion medium to form soluble carbohydrates and a phenolics liquid phase may take place while the cellulosic biomass solids are in a pressurized state. As used herein, the term "pressurized state" refers to a pressure that is greater than atmospheric pressure (1 bar). Heating a fluid phase digestion medium in a pressurized state may allow the normal boiling point of the digestion solvent to be exceeded, thereby allowing the rate of hydrothermal digestion to be increased relative to lower temperature digestion processes. In some embodiments, heating the cellulosic biomass solids and the fluid phase digestion medium may take place at a pressure of at least about 30 bar. In some embodiments, heating the cellulosic biomass solids and the fluid phase digestion medium may take place at a pressure of at least about 60 bar, or at a pressure of at least about 90 bar. In some embodiments, heating the cellulosic biomass solids and the fluid phase digestion medium may take place at a pressure ranging between about 30 bar and about 430 bar. In some embodiments, heating the cellulosic biomass solids and the fluid phase digestion medium may take place at a pressure ranging between about 50 bar and about 330 bar, or at a pressure ranging between about 70 bar and about 130 bar, or at a pressure ranging between about 30 bar and about 130 bar.

To facilitate a better understanding of the present invention, the following examples of preferred embodiments are given. In no way should the following examples be read to limit, or to define, the scope of the invention.

EXAMPLES

Example 1

Hydrothermal Digestion of Pine Softwood Minichips. A 100 mL Parr reactor was charged with 60 grams of 35% ethanol in deionized water solvent, 0.19 grams of potassium carbonate buffer, and 1.8 grams of slurry catalyst. The slurry catalyst was a sulfided nickel oxide promoted cobalt molybdate catalyst (DC-2534, Criterion Catalyst & Technologies L.P., containing 1-10% cobalt oxide and molybdenum trioxide (up to 30 wt %) on alumina, and less than 2% nickel), which was previously sulfided as described in United States Patent Application Publication 2010/0236988, incorporated herein by reference in its entirety. 6 grams of pine softwood minichips having nominal dimensions of 3 mm×4 mm×5 mm were then added to the reactor, which was then pressurized with 55 bar of hydrogen. The reactor was then heated at 190° C. for 1 hour, followed by heating at 250° C. for 4 hours. Thereafter, the reactor was cooled, and 6 grams of liquid product were removed by a 0.5 micron filtered dip tube. The reactor was then repressurized as above, and 8 subsequent cycles of heating and liquid product withdrawal were conducted. The final liquid product contained $C_3$-$C_6$ mono-oxygenated hydrocarbons and $C_2$-$C_3$ glycols. Residual ethanol and water were also present.

Example 2

Motion of Pine Softwood Minichips on an Inclined Surface. A glass tube 25 mm in diameter and 450 mm long was filled with deionized water and packed at one end with a 1.5 inch plug of southern pine softwood minichips (39% moisture) having nominal dimensions of 3 mm×4 mm×5 mm. The tube was then tilted until the plug of wood chips began to flow along the inclined plane. The onset of flow was observed at a tube angle of 29 degrees relative to horizontal at a flow velocity of 0.17 cm/sec. The wood slug assumed a flowing configuration having a bed height of less than about 0.6 cm, measured normal to the incline, and a slug length of greater than 25 cm.

Example 3

Motion of Pine Softwood Minichips on an Inclined Surface. Example 2 was repeated at an incline of 36 degrees relative to horizontal. The wood slug again assumed a flat configuration having a height less than 25% of the tube diameter. The observed flow rate was 0.56 cm/sec.

Example 4

Motion of Pine Softwood Minichips on an Inclined Surface. Example 2 was repeated at an incline of 39 degrees relative to horizontal. The observed flow rate was 1.1 cm/sec. The length to height aspect ratio of the slug was greater than 40:1.

Example 5

Motion of Pine Softwood Minichips in a Vertical Column of Water. Southern pine softwood minichips (39% moisture) having nominal dimensions of 3 mm×4 mm×5 mm were dropped into a 7.5 inch column of water in a 100 mL graduated cylinder, and the times needed for the chips to sink to the bottom of the column was determined. Times ranged up to 5 seconds, with an average time of about 4 seconds. For the average time of 4 seconds, the corresponding flow velocity was 4.97 cm/sec. Thus, by flowing a slug of wood chips along an inclined surface, a lower velocity may obtained than in free fall. In the absence of wall contact and at a 90 degree angle.

Therefore, present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods may also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

We claim:
1. A method comprising:
   introducing cellulosic biomass solids to a hydrothermal digestion unit comprising one or more inclined surfaces therein;
   introducing a fluid phase digestion medium containing a slurry catalyst to the hydrothermal digestion unit, the slurry catalyst being capable of activating molecular hydrogen;
   wherein, once introduced to the hydrothermal digestion unit, the cellulosic biomass solids, the fluid phase digestion medium, and the slurry catalyst descend along the one or more inclined surfaces;

supplying an upwardly directed flow of molecular hydrogen through the cellulosic biomass solids as they descend along the one or more inclined surfaces, the upwardly directed flow of molecular hydrogen being supplied from a source disposed along each inclined surface; and heating the cellulosic biomass solids as they descend along the one or more inclined surfaces in the presence of the slurry catalyst and the molecular hydrogen, thereby forming an alcoholic component derived from the cellulosic biomass solids.

2. The method of claim 1, wherein the one or more inclined surfaces are inclined at an angle ranging between about 5 degrees and about 85 degrees relative to horizontal.

3. The method of claim 1, wherein the cellulosic biomass solids are introduced to the hydrothermal digestion unit separately from the fluid phase digestion medium and the slurry catalyst.

4. The method of claim 1, further comprising:
removing at least a portion of the fluid phase digestion medium and the slurry catalyst from the hydrothermal digestion unit after they have descended the one or more inclined surfaces.

5. The method of claim 4, further comprising:
returning at least a portion of the fluid phase digestion medium and the slurry catalyst to the hydrothermal digestion unit.

6. The method of claim 5, wherein returning at least a portion of the fluid phase digestion medium and the slurry catalyst to the hydrothermal digestion unit comprises conveying the fluid phase digestion medium and the slurry catalyst to an uppermost inclined surface.

7. The method of claim 1, wherein the hydrothermal digestion unit comprises one or more inclined tubular elements.

8. The method of claim 7, wherein the inclined tubular elements are each inclined at an angle ranging between about 5 degrees and about 85 degrees relative to horizontal.

9. The method of claim 7, wherein the cellulosic biomass solids are introduced to the hydrothermal digestion unit separately from the fluid phase digestion medium and the slurry catalyst.

10. The method of claim 7, further comprising:
removing at least a portion of the fluid phase digestion medium and the slurry catalyst from the hydrothermal digestion unit after they have descended the one or more inclined tubular elements.

11. The method of claim 10, further comprising:
returning at least a portion of the fluid phase digestion medium and the slurry catalyst to the hydrothermal digestion unit.

12. The method of claim 11, wherein returning at least a portion of the fluid phase digestion medium and the slurry catalyst to the hydrothermal digestion unit comprises conveying the fluid phase digestion medium and the slurry catalyst to an uppermost inclined tubular element.

13. The method of claim 7, wherein the hydrothermal digestion unit comprises a plurality of inclined tubular elements that are fluidly connected to one another in series and vertically spaced apart from one another.

14. The method of claim 13, wherein the hydrothermal digestion unit further comprises a vertical fluid connection adjoining an upper inclined tubular element to a lower inclined tubular element.

15. The method of claim 13, further comprising:
transferring molecular hydrogen from a lower inclined tubular element to an upper inclined tubular element.

16. The method of claim 7, wherein the upwardly directed flow of molecular hydrogen through the cellulosic biomass solids is supplied from a gas distribution system longitudinally disposed within each inclined tubular element along its length, a feed for the gas distribution system entering each inclined tubular element at a level above that of the fluid phase digestion medium therein.

17. The method of claim 16, wherein the gas distribution system is disposed substantially parallel to the incline of each inclined tubular element and is located within the lower 40% of each inclined tubular element, as measured along a line extending normal to the incline and intersecting an opposing surface thereto.

18. The method of claim 1, wherein the fluid phase digestion medium comprises an organic solvent and water.

19. The method of claim 1, wherein the slurry catalyst comprises a poison-tolerant catalyst.

20. The method of claim 19, wherein the poison-tolerant catalyst comprises a sulfided catalyst.

21. A method comprising:
introducing cellulosic biomass solids to a hydrothermal digestion unit comprising a plurality of inclined tubular elements that are fluidly connected to one another in series and vertically spaced apart from one another;

introducing a fluid phase digestion medium containing a slurry catalyst to the hydrothermal digestion unit, the slurry catalyst being capable of activating molecular hydrogen;

wherein, once introduced to the hydrothermal digestion unit, the cellulosic biomass solids, the fluid phase digestion medium, and the slurry catalyst descend along the inclined tubular elements;

supplying an upwardly directed flow of molecular hydrogen through the cellulosic biomass solids as they descend along the inclined tubular elements, the upwardly directed flow of molecular hydrogen being supplied from a source disposed longitudinally along each inclined tubular element;

transferring molecular hydrogen from a lower inclined tubular element to an upper inclined tubular element; and heating the cellulosic biomass solids as they descend along the inclined tubular elements in the presence of the slurry catalyst and the molecular hydrogen, thereby forming an alcoholic component derived from the cellulosic biomass solids.

22. The method of claim 21, wherein the inclined tubular elements are each inclined at an angle ranging between about 5 degrees and about 85 degrees relative to horizontal.

23. The method of claim 21, wherein the cellulosic biomass solids are introduced to the hydrothermal digestion unit separately from the fluid phase digestion medium and the slurry catalyst.

24. The method of claim 21, further comprising:
removing at least a portion of the fluid phase digestion medium and the slurry catalyst from the hydrothermal digestion unit after they have descended the plurality of inclined tubular elements.

25. The method of claim 24, further comprising:
returning at least a portion of the fluid phase digestion medium and the slurry catalyst to the hydrothermal digestion unit.

26. The method of claim 25, wherein returning at least a portion of the fluid phase digestion medium and the slurry catalyst to the hydrothermal digestion unit comprises conveying the fluid phase digestion medium and the slurry catalyst from a lowermost inclined tubular element to an uppermost inclined tubular element.

27. The method of claim 21, wherein the hydrothermal digestion unit further comprises a vertical fluid connection adjoining an upper inclined tubular element to a lower inclined tubular element.

28. The method of claim 21, wherein the upwardly directed flow of molecular hydrogen through the cellulosic biomass solids is supplied from a gas distribution system longitudinally disposed within each inclined tubular element along its length, a feed for the gas distribution system entering each inclined tubular element at a level above that of the fluid phase digestion medium therein.

29. The method of claim 28, wherein the gas distribution system is disposed substantially parallel to the incline of each inclined tubular element and is located within the lower 40% of each inclined tubular element, as measured along a line extending normal to the incline and intersecting an opposing surface thereto.

30. The method of claim 21, wherein the fluid phase digestion medium comprises an organic solvent and water.

31. The method of claim 21, wherein the slurry catalyst comprises a poison-tolerant catalyst.

32. The method of claim 31, wherein the poison-tolerant catalyst comprises a sulfided catalyst.

\* \* \* \* \*